United States Patent
Burbank et al.

(10) Patent No.: US 7,686,778 B2
(45) Date of Patent: Mar. 30, 2010

(54) WASTE BALANCING FOR EXTRACORPOREAL BLOOD TREATMENT SYSTEMS

(75) Inventors: Jeffrey H. Burbank, Boxford, MA (US); James M. Brugger, Newburyport, MA (US)

(73) Assignee: NxStage Medical, Inc., Lawrence, MA (US)

( * ) Notice: Subject to any disclaimer, the term of this patent is extended or adjusted under 35 U.S.C. 154(b) by 905 days.

(21) Appl. No.: 10/544,124

(22) PCT Filed: Jan. 14, 2004

(86) PCT No.: PCT/US2004/000921

§ 371 (c)(1),
(2), (4) Date: Aug. 7, 2006

(87) PCT Pub. No.: WO2004/066121

PCT Pub. Date: Aug. 5, 2004

(65) Prior Publication Data

US 2007/0038191 A1 Feb. 15, 2007

Related U.S. Application Data

(60) Provisional application No. 60/440,176, filed on Jan. 15, 2003.

(51) Int. Cl.
*A61M 37/00* (2006.01)
*C02F 1/44* (2006.01)

(52) U.S. Cl. .................. 604/5.04; 604/6.09; 210/645
(58) Field of Classification Search ............ 604/5.04, 604/6.09; 210/645, 646
See application file for complete search history.

(56) References Cited

U.S. PATENT DOCUMENTS

| | | | |
|---|---|---|---|
| 4,275,726 A | 6/1981 | Schael | |
| 4,479,760 A | 10/1984 | Bilstad et al. | |
| 4,479,761 A | 10/1984 | Bilstad et al. | |
| 4,479,762 A | 10/1984 | Bilstad et al. | |
| 4,576,603 A | 3/1986 | Moss | |
| 4,596,550 A | 6/1986 | Troutner | |
| 4,610,781 A | 9/1986 | Bilstad et al. | |
| 4,614,590 A | 9/1986 | Rath et al. | |
| 4,617,115 A | 10/1986 | Vantard | |
| 4,629,448 A | 12/1986 | Carlsson et al. | |
| 4,661,246 A | 4/1987 | Ash et al. | |
| 4,666,598 A | 5/1987 | Heath et al. | |
| 4,670,007 A | 6/1987 | Wheeldon et al. | |

(Continued)

OTHER PUBLICATIONS

International Search Report (PCT/US04/00921).

(Continued)

*Primary Examiner*—Leslie R Deak
(74) *Attorney, Agent, or Firm*—Mark A. Catan; Miles & Stockbridge P.C.

(57) ABSTRACT

One or more waste balancing systems may be used in a fluid circulating system for medical use. The fluid circulating system may be part of a blood treatment system for a patient suffering renal failure. A waste balancing system may include a pressure element operable to maintain a constant fluid pressure created by the combined weight of waste removed from a patient and replacement fluid for providing to a patient. Multiple evaluation characteristics or control parameters may be evaluated or controlled for safety and accuracy. At least part of the waste balancing system may be incorporated into a disposable cartridge.

12 Claims, 27 Drawing Sheets

U.S. PATENT DOCUMENTS

| | | | |
|---|---|---|---|
| 4,702,829 | A | 10/1987 | Polaschegg et al. |
| 4,711,715 | A | 12/1987 | Polaschegg |
| 4,713,171 | A | 12/1987 | Polaschegg |
| 4,728,433 | A | 3/1988 | Buck et al. |
| 4,765,888 | A | 8/1988 | Barthe et al. |
| 4,770,787 | A | 9/1988 | Heath et al. |
| 4,857,199 | A | 8/1989 | Cortial |
| 4,894,150 | A | 1/1990 | Schurek |
| 4,894,164 | A | 1/1990 | Polaschegg |
| 4,899,057 | A | 2/1990 | Koji |
| 4,909,931 | A | 3/1990 | Bibi |
| 4,923,598 | A | 5/1990 | Schal |
| 4,950,395 | A | 8/1990 | Richalley |
| 4,997,570 | A | 3/1991 | Polaschegg |
| 5,194,157 | A | 3/1993 | Ghezzi et al. |
| 5,211,849 | A | 5/1993 | Kitaevich et al. |
| 5,247,434 | A * | 9/1993 | Peterson et al. .............. 700/83 |
| 5,277,820 | A | 1/1994 | Ash |
| 5,344,568 | A | 9/1994 | Kitaevich et al. |
| 5,399,157 | A | 3/1995 | Goux et al. |
| 5,441,636 | A | 8/1995 | Chevallet et al. |
| 5,470,483 | A | 11/1995 | Bene et al. |
| 5,476,592 | A | 12/1995 | Simard |
| 5,484,397 | A | 1/1996 | Twardowski |
| 5,486,286 | A | 1/1996 | Peterson et al. |
| 5,487,827 | A | 1/1996 | Peterson et al. |
| 5,518,623 | A | 5/1996 | Keshaviah et al. |
| 5,522,998 | A | 6/1996 | Polaschegg |
| 5,569,463 | A | 10/1996 | Helmus et al. |
| 5,616,305 | A | 4/1997 | Mathieu |
| 5,641,405 | A | 6/1997 | Keshaviah et al. |
| 5,662,806 | A | 9/1997 | Keshaviah et al. |
| 5,679,245 | A | 10/1997 | Manica |
| 5,698,090 | A | 12/1997 | Bene et al. |
| 5,702,597 | A | 12/1997 | Cehvallet et al. |
| 5,725,776 | A | 3/1998 | Kenley et al. |
| 5,744,027 | A | 4/1998 | Connell et al. |
| 5,762,805 | A | 6/1998 | Truitt et al. |
| 5,776,345 | A | 7/1998 | Truitt et al. |
| 5,808,181 | A | 9/1998 | Wamsiedler et al. |
| 5,836,908 | A | 11/1998 | Beden et al. |
| 5,846,419 | A | 12/1998 | Nederlof |
| 5,863,421 | A | 1/1999 | Peter et al. |
| 5,871,694 | A | 2/1999 | Beden et al. |
| 5,919,154 | A | 7/1999 | Toavs et al. |
| 5,951,870 | A | 9/1999 | Utterberg |
| 6,039,877 | A | 3/2000 | Chevallet et al. |
| 6,042,784 | A | 3/2000 | Wamsiedler et al. |
| 6,044,691 | A | 4/2000 | Kenley et al. |
| 6,066,261 | A | 5/2000 | Spickermann |
| 6,979,309 | B2 | 12/2005 | Burbank et al. |
| 2001/0037079 | A1 * | 11/2001 | Burbank et al. ............ 604/6.09 |
| 2003/0217962 | A1 | 11/2003 | Childers et al. |
| 2004/0050789 | A1 | 3/2004 | Ash |
| 2004/0133145 | A1 | 7/2004 | Bene |
| 2004/0215129 | A1 | 10/2004 | Edgson et al. |
| 2004/0267184 | A1 | 12/2004 | Burbank et al. |
| 2005/0020958 | A1 | 1/2005 | Paolini et al. |
| 2005/0043665 | A1 | 2/2005 | Vinci et al. |
| 2005/0045540 | A1 | 3/2005 | Connell et al. |
| 2005/0061740 | A1 | 3/2005 | Felding et al. |
| 2005/0065459 | A1 | 3/2005 | Zhang et al. |
| 2005/0070837 | A1 | 3/2005 | Ferrarini et al. |
| 2005/0082210 | A1 | 4/2005 | Favre |
| 2005/0085760 | A1 | 4/2005 | Ware et al. |
| 2005/0090774 | A1 | 4/2005 | Tonelli et al. |
| 2005/0126998 | A1 | 6/2005 | Childers |
| 2005/0131331 | A1 | 6/2005 | Kelly et al. |
| 2005/0131332 | A1 | 6/2005 | Kelly et al. |
| 2005/0171475 | A1 | 8/2005 | Delnevo |
| 2005/0197612 | A1 | 9/2005 | Levin et al. |
| 2005/0205476 | A1 | 9/2005 | Chevallet et al. |
| 2005/0209563 | A1 | 9/2005 | Hopping et al. |
| 2005/0230292 | A1 | 10/2005 | Beden et al. |
| 2005/0234384 | A1 | 10/2005 | Westberg et al. |
| 2005/0234385 | A1 | 10/2005 | Vandlik et al. |
| 2005/0251086 | A1 | 11/2005 | Sternby |

OTHER PUBLICATIONS

International Preliminary Report on Patentability (PCT/US04/00921).

* cited by examiner

WASTE BALANCING FOR EXTRACORPOREAL BLOOD TREATMENT SYSTEMS

CROSS REFERENCE TO RELATED APPLICATIONS

The present application is a national stage of PCT/US2004/000921, filed Jan. 14, 2004, which claims the benefit of U.S. Provisional Application No. 60/440,176, filed Jan. 15, 2003.

A fluid circulating system for medical use may evaluate a characteristic relating to waste removed from a patient and on that basis control a replacement fluid parameter. The waste characteristic evaluated in the present invention may be weight, volume, flow rate, concentration, and/or others, for example. Similarly, the replacement fluid parameter controlled may be weight, volume, flow rate, concentration, and/or others, for example. More than one waste characteristic may be evaluated to provide a redundant check on accuracy. Likewise, more than one replacement fluid parameter may be controlled. The control may be implemented, in a system for treating renal failure, to balance waste removed from a patient's blood against replacement fluid added to the patient's blood, for example. The control may be based on a desired filtration factor or ultrafiltration amount, for example.

DETAILED DESCRIPTION OF EXEMPLARY EMBODIMENTS

Figure 1:
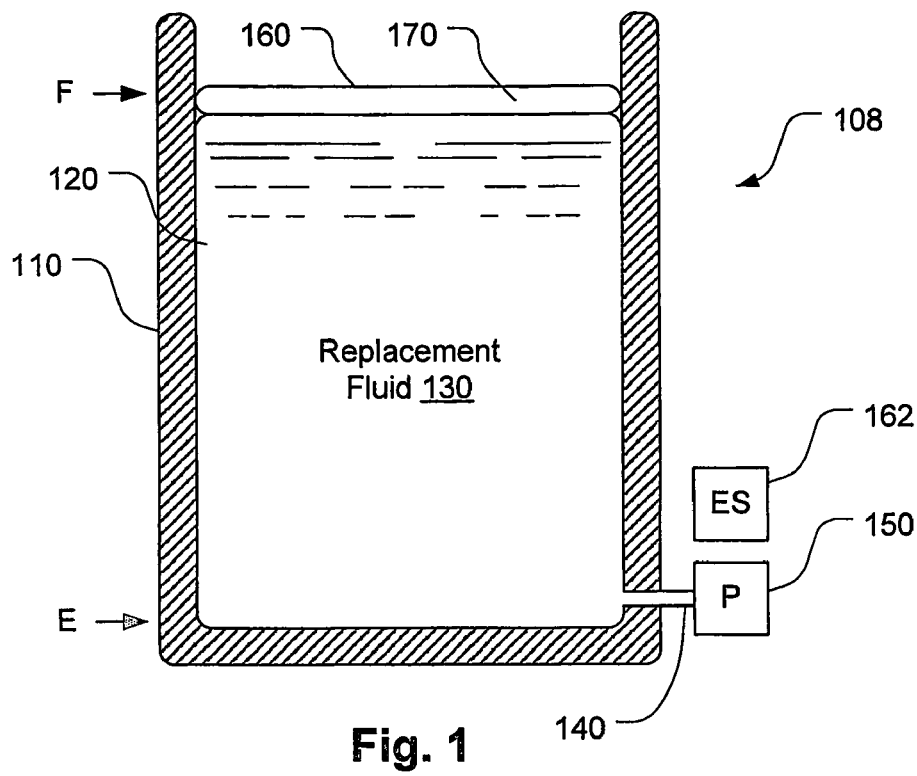
FIG. 1 is a diagrammatic depiction of a waste balancing system for use in a fluid circulating system.

An example of a waste balancing system for use in a fluid circulating system is shown in FIG. 1. Waste balancing system 108 includes container 110, flexible bag 120, valve 140, pressure element 150, and flexible bag 160. Container 110 is rigid and defines an interior volume, height, and width. Container 110 accommodates flexible bag 120. Flexible bag 120 may contain replacement fluid for a patient undergoing hemofiltration, for example. Flexible bag 120 is depicted in a full state in FIG. 1. That is, flexible bag 120 is filled with fluid 130 up to the maximum capacity of flexible bag 120. The height of flexible bag 120 varies with the amount of fluid it contains. In particular, the height of flexible bag 120 may vary directly in proportion to the amount of fluid it contains, with no air permitted in flexible bag 120. Valve 140 is located at the bottom of container 110 and defines a passage from the interior of flexible bag 120 to the exterior of container 110. Valve 140 permits fluid 130 to communicate with pressure element 150.

A second flexible bag 160 is placed on top of flexible bag 120. Flexible bag 160 may have characteristics similar to flexible bag 120. In particular, the height of flexible bag 160 may vary with the amount of waste contained by flexible bag 160, in the same proportion that the height of flexible bag 120 varies with the amount of fluid contained by flexible bag 120. Flexible bag 160 may be configured to receive waste, but is shown in FIG. 1 as being empty.

Pressure element 150 permits replacement fluid 130 to flow out of container 110 through valve 140 only when replacement fluid 130 at valve 140 is subject to a predetermined amount of fluid pressure. That predetermined amount may be equal to the pressure experienced at valve 140 when flexible bag 120 is full and flexible bag 160 is empty. This full state is represented by the level labeled "F" in FIG. 1. In that case, pressure element 150 only permits fluid 130 to flow out of container 110 when fluid 130 at valve 140 is subject to fluid pressure greater than that caused by the weight of fluid 130 when flexible bag 120 is full and flexible bag 160 is empty.

Waste balancing system 108 may have an empty sensor 162. Empty sensor 162 is designed and adapted to sense when replacement fluid 130 has been depleted to or below the empty level "E" shown in FIG. 1. Empty sensor 162 may be located near the bottom of container 110 at the approximate height of level E, near pressure element 150, or elsewhere in a fluid circulating system.

Empty sensor 162 may include a waste bag sensor designed to sense when the flexible bag 160 has expanded with waste to the point where the bottom of flexible bag 160 has dropped from the F position shown in FIG. 1 down to level E. Such a waste bag sensor may include an optical sensor set to distinguish the optical characteristics of waste from those of replacement fluid. In that case, the optical sensor may be located near or within container 110 at level E. Alternatively, the waste bag sensor may include a mechanical sensor cooperating between container 110, flexible bag 160, and/or flexible bag 120. In that case, the mechanical sensor may be located at least partly within container 110 and may sense when the bottom of flexible bag 160 and/or the top of flexible bag 120 has dropped to level E.

Alternatively, empty sensor 162 may include a flow sensor designed to sense flow of replacement fluid out of container 110. Such a flow sensor may be located at valve 140 or downstream thereof. The flow sensor may include a flow meter designed to measure the flow amount of replacement fluid that has exited flexible bag 120. This flow amount would be compared to the available amount of replacement fluid that was initially available for exiting flexible bag 120. For example, the available amount may be the capacity of flexible bag 120 minus any amount of replacement fluid 130 that remains when flexible bag 120 is reduced to level E or otherwise considered empty. This comparison may be done automatically with a controller.

Alternatively, a flow sensor may comprise a pump sensor designed to sense operation of a pump downstream of valve 140. Such a pump sensor may for example sense the amount of time the pump is pumping replacement fluid exiting flexible bag 120 or the number of cycles (e.g. rotations) of a positive displacement pump or prime mover. With knowledge of the flow rate associated with the pump, a pumping period or number of cycles may be identified to approximate that required to pump all of the available replacement fluid 130 out of flexible bag 120. The pump may operate continuously or intermittently. When the pump has operated for an aggregate amount of time equal to or slightly less than the pumping period, the pump sensor would indicate that flexible bag 120 should be considered empty.

Empty sensor 162 may signal an alarm to indicate that flexible bag 120 is empty. The alarm may be audible, visual, or electronic. An electronic alarm could be conveyed to a circulation system controller for appropriate action. The circulation system controller may be an automatic system co-located with waste balancing system 108 or may be located remotely.

Figure 2:
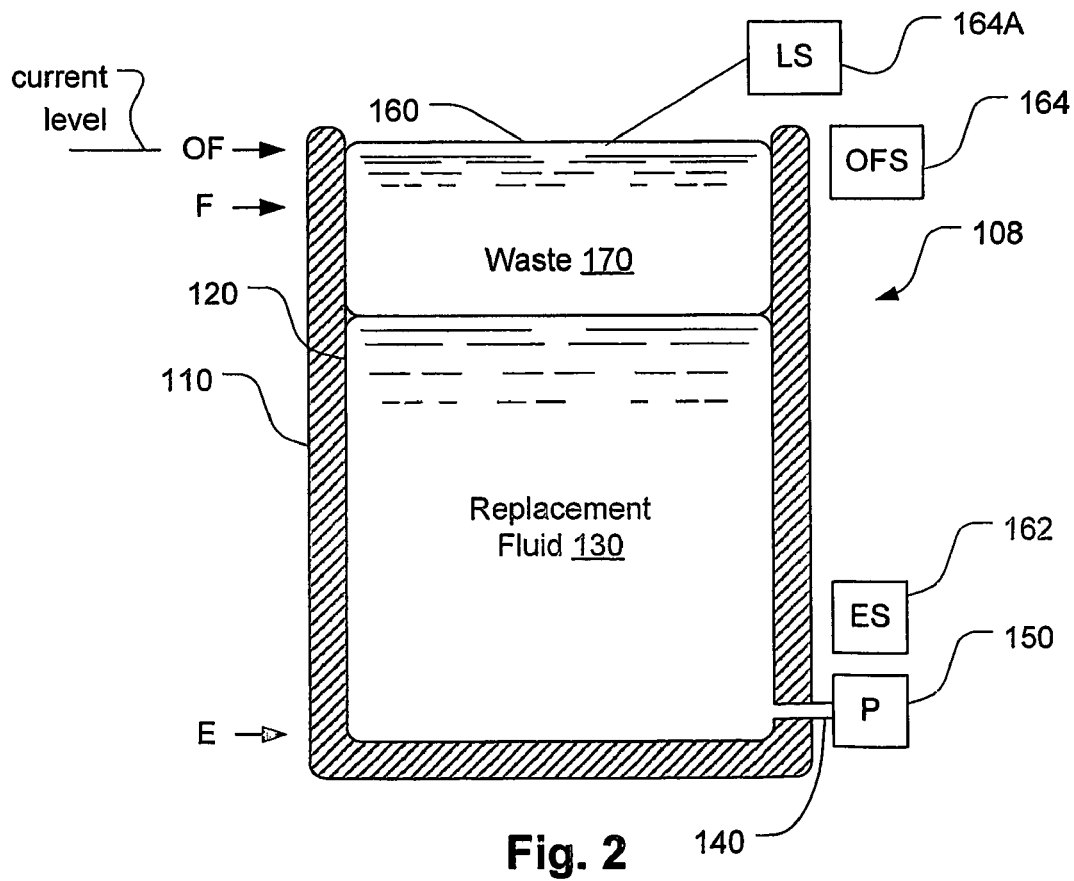
FIGS. 2, 3, 4, and 5 are illustrations of various possible states of the waste balancing system of FIG. 1.

FIG. 2 shows waste balancing system 108 in a temporary state in which waste 170 has just been added to flexible bag 160, but before pressure element 150 has permitted passage of any replacement fluid 130 from flexible bag 120. This over-full state is represented by the level labeled "O.F." in FIG. 2. This state may be merely instantaneous, lasting only long enough for pressure element 150 to sense the additional pressure caused by the addition of waste 170 and to permit passage of replacement fluid.

Waste balancing system 108 may include over-full sensor 164. Over-full sensor 164 may be used to sense the accumulation of waste in flexible bag 160. When over-full sensor 164 senses that the top of flexible bag 160 has risen to level O.F., over-full sensor may indicate that condition to a controller which in turn may control pressure element 150 to permit passage of replacement fluid 130 through valve 140. This sensing and control may replace or supplement the sensing function of pressure element 150. When that function is replaced, pressure element 150 need not sense the pressure; it merely needs to control the pressure under control of the controller. When that function is supplemented, the over-full sensor and the controller may act as a redundant check on the pressure sensing function of pressure element 150 to ensure accuracy. The over-full sensor may signal an alarm when it senses that the combined height of flexible bags 120 and 160 reaches the O.F. level. In a system designed to have the combined height normally below the O.F. level, the alarm may alert the patient, an operator, or a remote monitor of possible malfunction.

Figure 3:
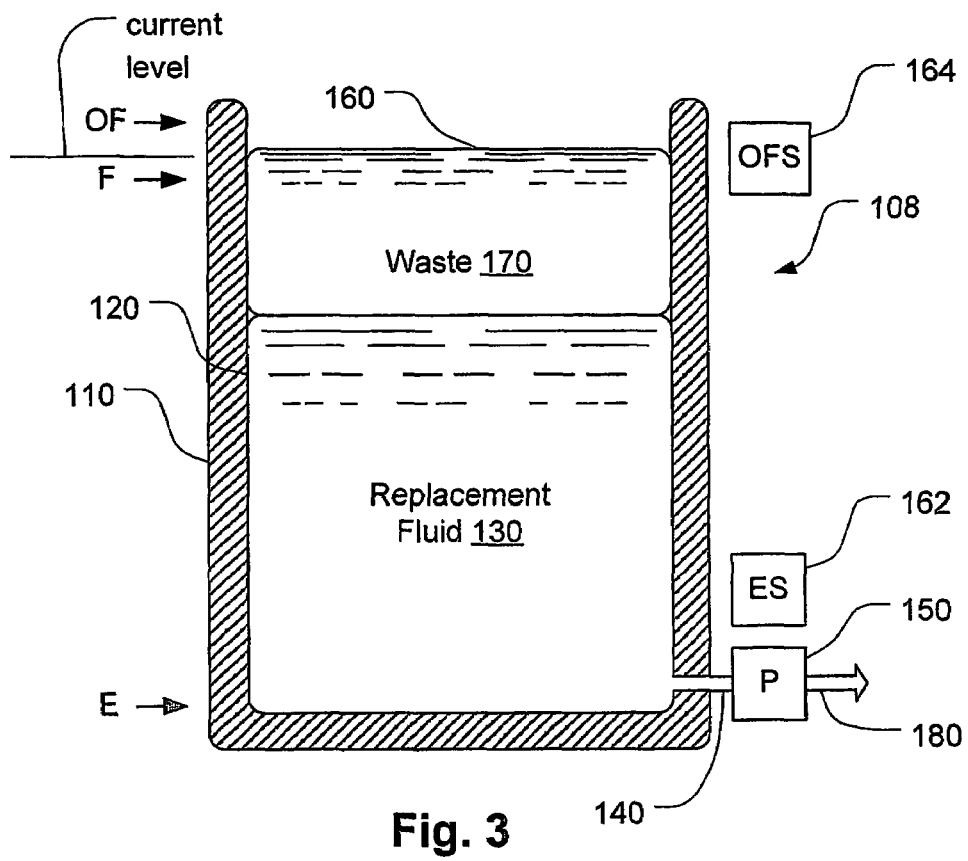

FIG. 3 shows an instantaneous state in which pressure element 150 has sensed the additional pressure caused by waste 170 in flexible bag 160 and in response has permitted some of replacement fluid 130 to flow out of container 110 as flow 180. Flow 180 may be directed to a patient in need of replacement fluid. In this instantaneous state, the combined height of flexible bag 120 and flexible bag 160 in container 110 is above the F level but is below the O.F. level described in connection with FIG. 2. Flow 180 continues until the combined height of flexible bag 120 and flexible bag 160 has been reduced again to F.

Figure 4:
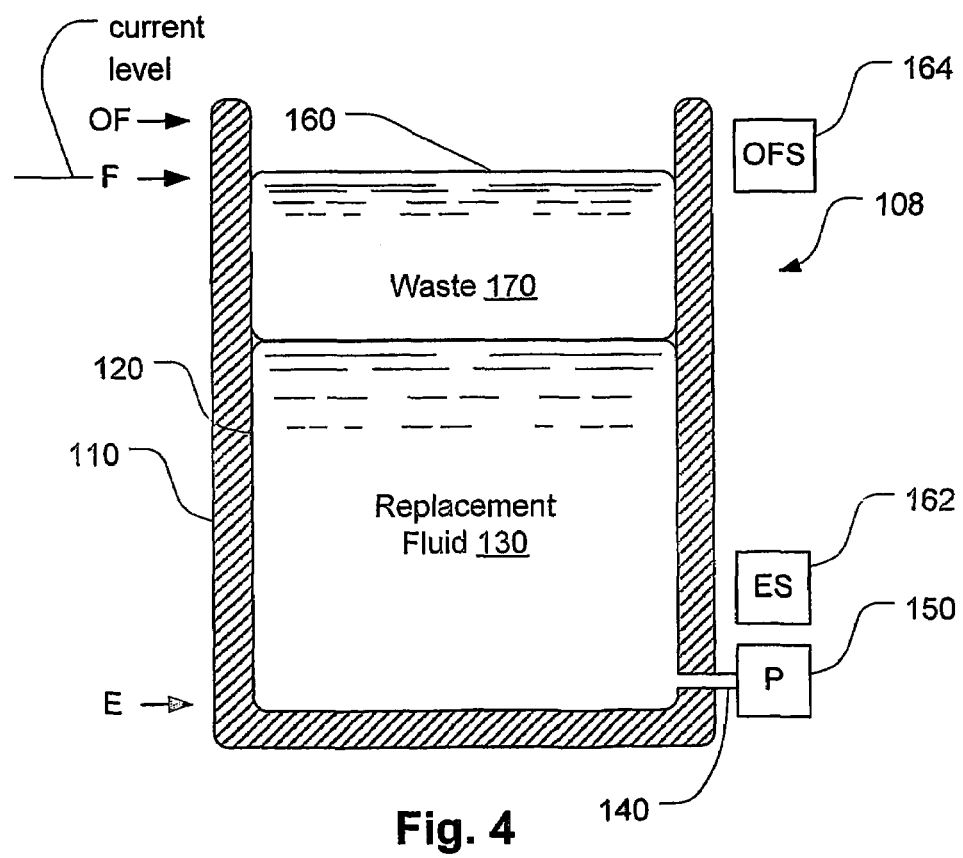

FIG. 4 shows a stable state following the state shown in FIG. 3. In this stable state, the combined height of flexible bag 120 and flexible bag 160 has been reduced again to F, causing flow 180 to cease.

Note that the above embodiment may employ a level sensor 164A instead of pressure sensing (by means of pressure element 150) as a means for determining whether the volume of replacement fluid sent to the patient is equal to the volume of waste withdrawn. According to the foregoing description, waste balancing system 108 may be controlled to supply replacement fluid corresponding to a characteristic of the removed waste. The characteristic may be volume (when a level sensor is used) and/or mass (when pressure element 150 senses pressure).

Figure 5:
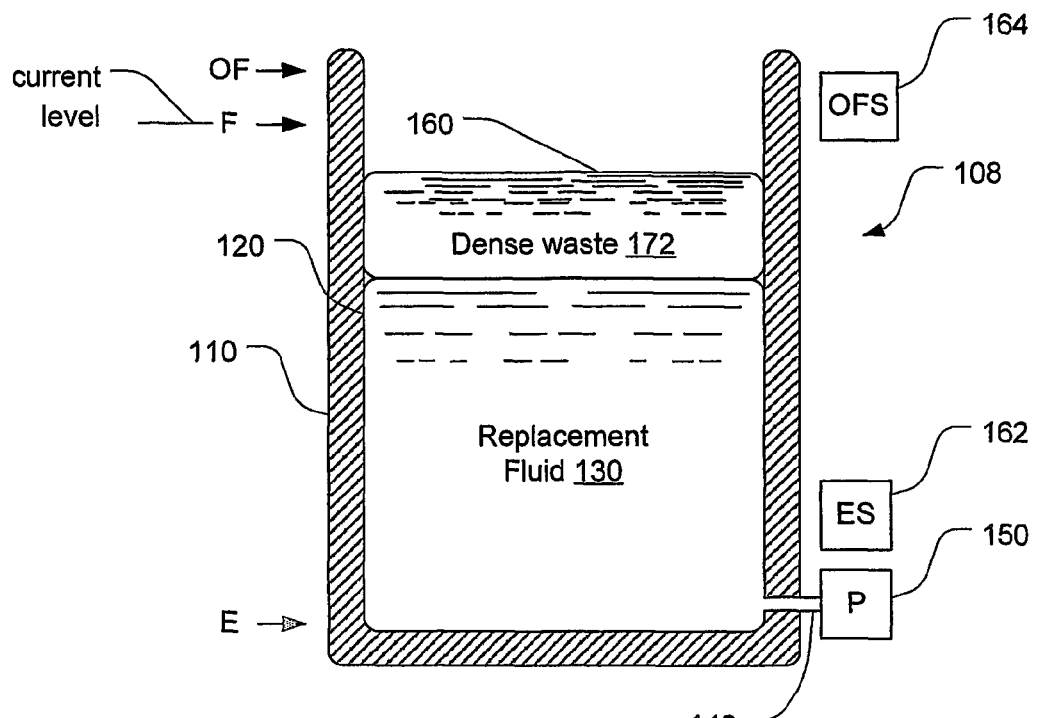

For example, it may be appropriate to control replacement fluid based on waste mass if the density of the removed waste may be variable or different than that of the replacement fluid. FIG. 5 shows a stable state for waste balancing system 108 after heavy waste 172 has been added to flexible bag 160. In this example, heavy waste 172 has higher density than replacement fluid 130. The pressure at valve 140 is the same as that shown in FIG. 1 and FIG. 4. Although the combined height of flexible bag 120 and flexible bag 160 is lower than the F level, the pressure at valve 140 has been maintained because heavy waste 172 has higher density than replacement fluid 130. Thus, the state shown in FIG. 5 may be reached from the state shown in FIG. 1 by adding heavy waste 172 and permitting pressure element 150 to maintain the fluid pressure at valve 140 by releasing some of replacement fluid 130 through valve 140. The example of FIG. 5 may be used to provide a patient with replacement fluid in an amount determined on the basis of the mass of removed waste.

Figure 6:
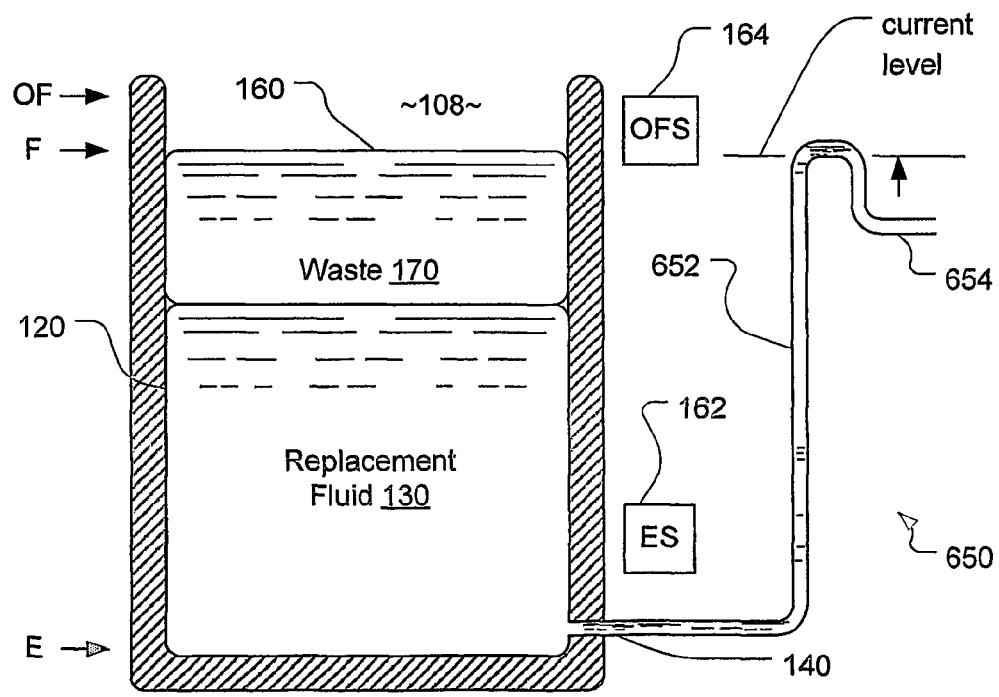
FIGS. 6, 8, and 9 are diagrammatic depictions of the waste balancing system of FIG. 1 incorporating various pressure elements.

FIG. 6 depicts an exemplary pressure element that may be used in conjunction with waste balancing system 108. Pressure element 650 consists of conduit 652, which rises to whatever height is necessary to maintain a desired pressure at valve 140. For example, conduit 652 is shown rising to a height corresponding to level F. This height may be fixed during manufacture of waste balancing system 108.

Alternatively, the height of conduit 652 in FIG. 6 may be adjustable. The proper height of conduit 652 may be determined by first raising conduit 652 to a starting height well above F. Second, flexible bag 120, full of replacement fluid 130 as shown, is inserted into container 110 along with flexible bag 160 in its empty state. Third, conduit 652 is then gradually lowered from the starting height to the height at which replacement fluid 130 first begins to flow out of conduit mouth 654. Fourth, conduit 652 is fixed at that first-flow height for operation of waste balancing system 108.

Figure 7:
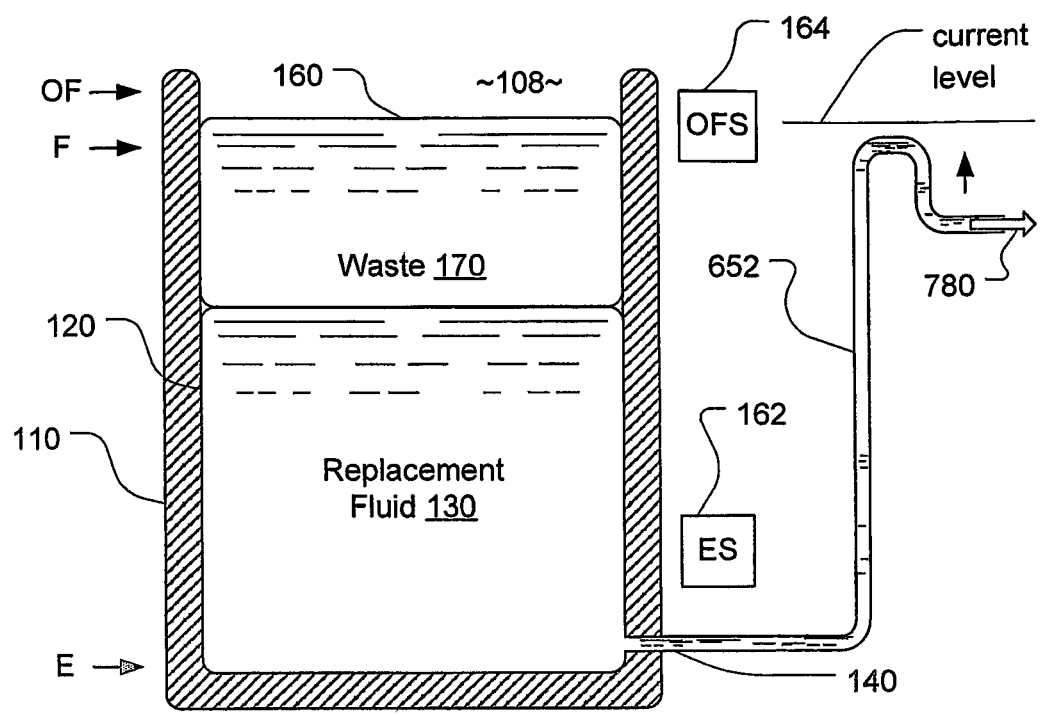
FIG. 7 is an illustration of a possible state of the system shown in FIG. 6.

FIG. 7 illustrates the pressure element of FIG. 6 in an instantaneous state after addition of waste 170 into flexible bag 160 bears down on flexible bag 120. In this state, pressure element 650 has sensed the additional pressure caused by waste 170 in flexible bag 160 and in response has permitted some of replacement fluid 130 to flow out of container 110 as flow 780. Flow 780 may be directed to a patient in need of replacement fluid. In this instantaneous state, the combined height of flexible bag 120 and flexible bag 160 in container 110 is above the F level but is below the O.F. level described in connection with FIG. 2. Flow 780 continues until the combined height of flexible bag 120 and flexible bag 160 has been reduced again to F.

Figure 8:
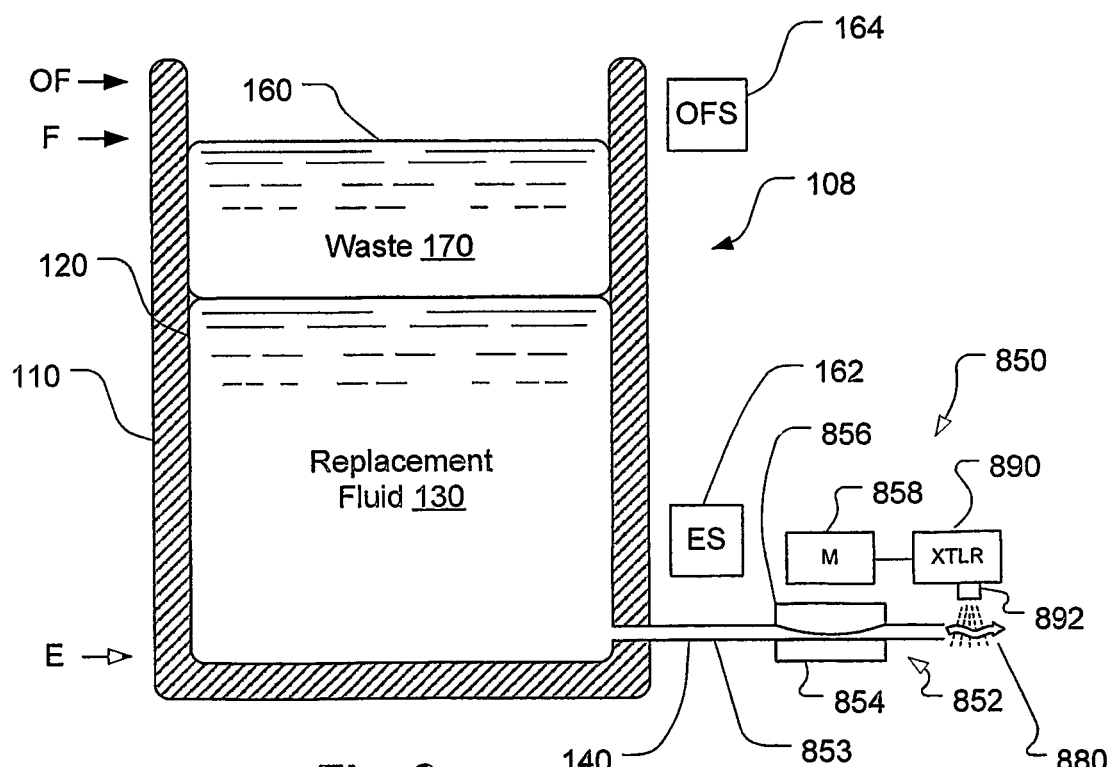

FIG. 8 depicts another exemplary pressure element for use in conjunction with waste balancing system 108. Pressure element 850 consists of clamp 852, conduit 853, and stepper motor 858. Clamp 852 comprises clamping elements 854 and 856 which cooperate to squeeze conduit 853 with a certain amount of force. The amount of force is that necessary to maintain desired fluid pressure at valve 140 as described above.

For example, the force of clamp 852 in FIG. 8 may be adjustable. Stepper motor 858 may be operated to cause clamp 852 to squeeze conduit 853 with various amounts of force. An operator installing waste balancing system 108 in its place of operation, such as a home, may first apply a very high amount of force squeezing conduit 853. Second, the operator may place flexible bag 120 in its full state into container 110, along with flexible bag 160 in an empty state. Third, the operator may gradually reduce the amount of force squeezing conduit 853 by adjusting stepper motor 858 until replacement fluid 130 starts to be released as flow 880. Fourth, the amount of force is fixed at that first-flow amount of force for operation of waste balancing system 108.

Instead of using an operator, this process may be carried out automatically with controller 890. Controller 890 may control stepper motor 858 to gradually reduce the amount of force squeezing conduit 853 until optical sensor 892 senses when replacement fluid 130 is first released as flow 880. Controller 890 may control stepper motor 858 to squeeze conduit 853 with that first-flow amount of force during operation of waste balancing system 108, thereby maintaining the desired pressure at valve 140.

Controller 890 may function as the circulation system controller referenced above in connection with FIG. 1.

Alternatively, stepper motor 858, controller 890, and optical sensor 892 may be omitted and the force of clamp 852 may be set mechanically. For example, the amount of force used to squeeze conduit 853 may be predetermined during manufacture of waste balancing system 108 and fixed by applying clamp 852 to conduit 853 with the predetermined amount of force either during manufacture or installation. Or, the amount of force used to squeeze conduit 853 may be mechanically adjustable, for example.

In the case of a mechanically adjustable clamp, an operator installing waste balancing system 108 in its place of operation such as a home, may first apply a very high amount of force squeezing conduit 853. Second, the operator may place flexible bag 120 in its full state into container 110, along with flexible bag 160 in an empty state. Third, the operator may gradually reduce the amount of force squeezing conduit 853 by mechanically adjusting clamp 852 until replacement fluid 130 starts to be released as flow 880. Fourth, the amount of force is fixed at that first-flow amount of force for operation of waste balancing system 108.

Figure 9A:
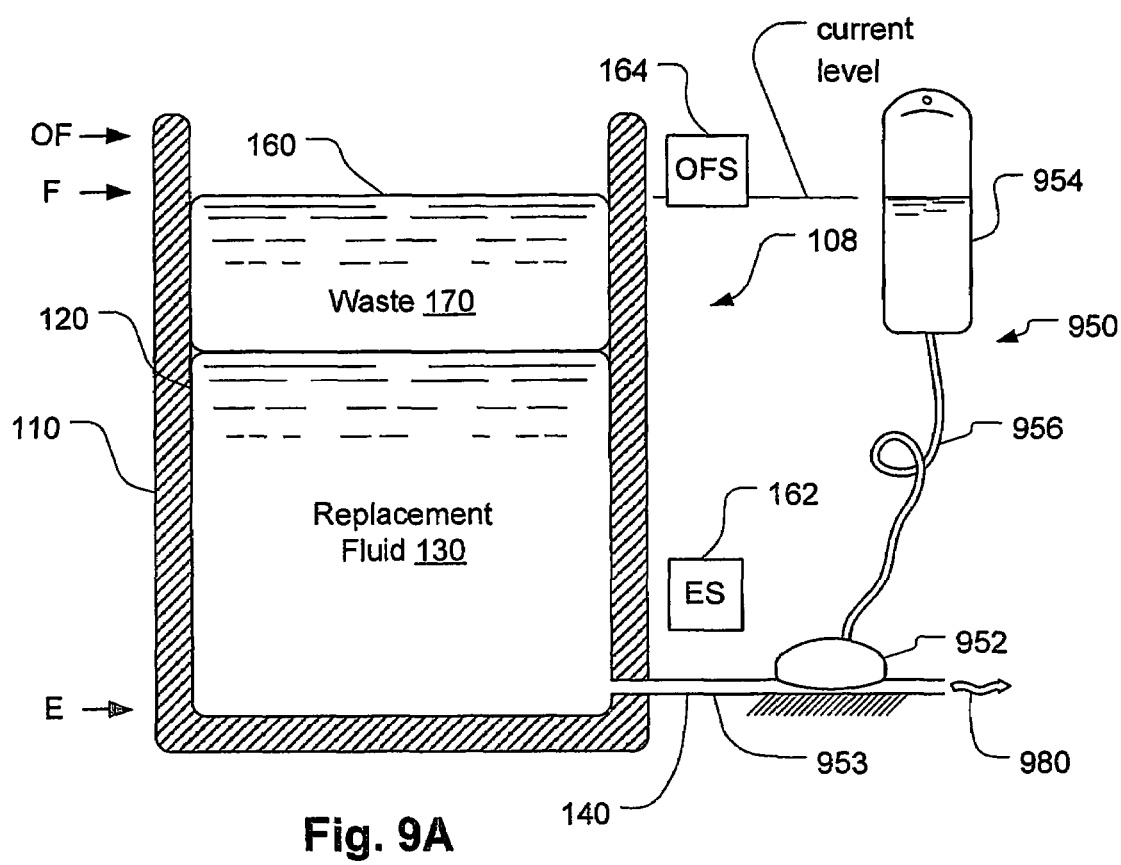
Figure 9B:
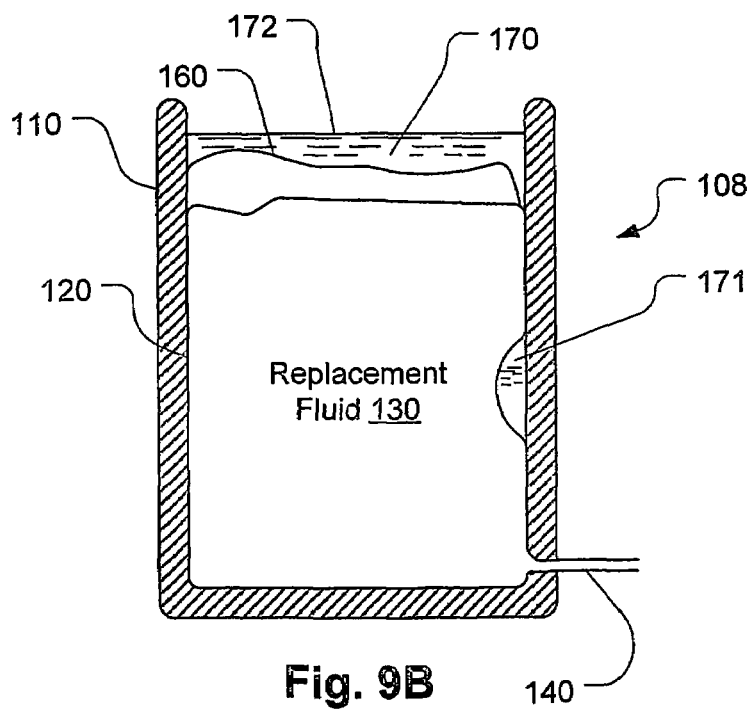

FIG. 9 shows another alternative pressure element comparable to that described in connection with FIG. 8. In FIG. 9, pressure element 950 consists of pressure bag 954 in fluid communication with pressure body 952 through pressure conduit 956. The weight of liquid in pressure bag 954 and the height of pressure bag 954 determines the pressure applied by pressure body 952 to squeeze conduit 953. Thus, the force used to squeeze conduit 953 may be adjusted by varying the amount of liquid in pressure bag 954 and/or the height of pressure bag 954. The appropriate amount of force may be determined by detecting when replacement fluid 130 is first released as flow 980 through valve 140 in like manner described above.

Figure 10:
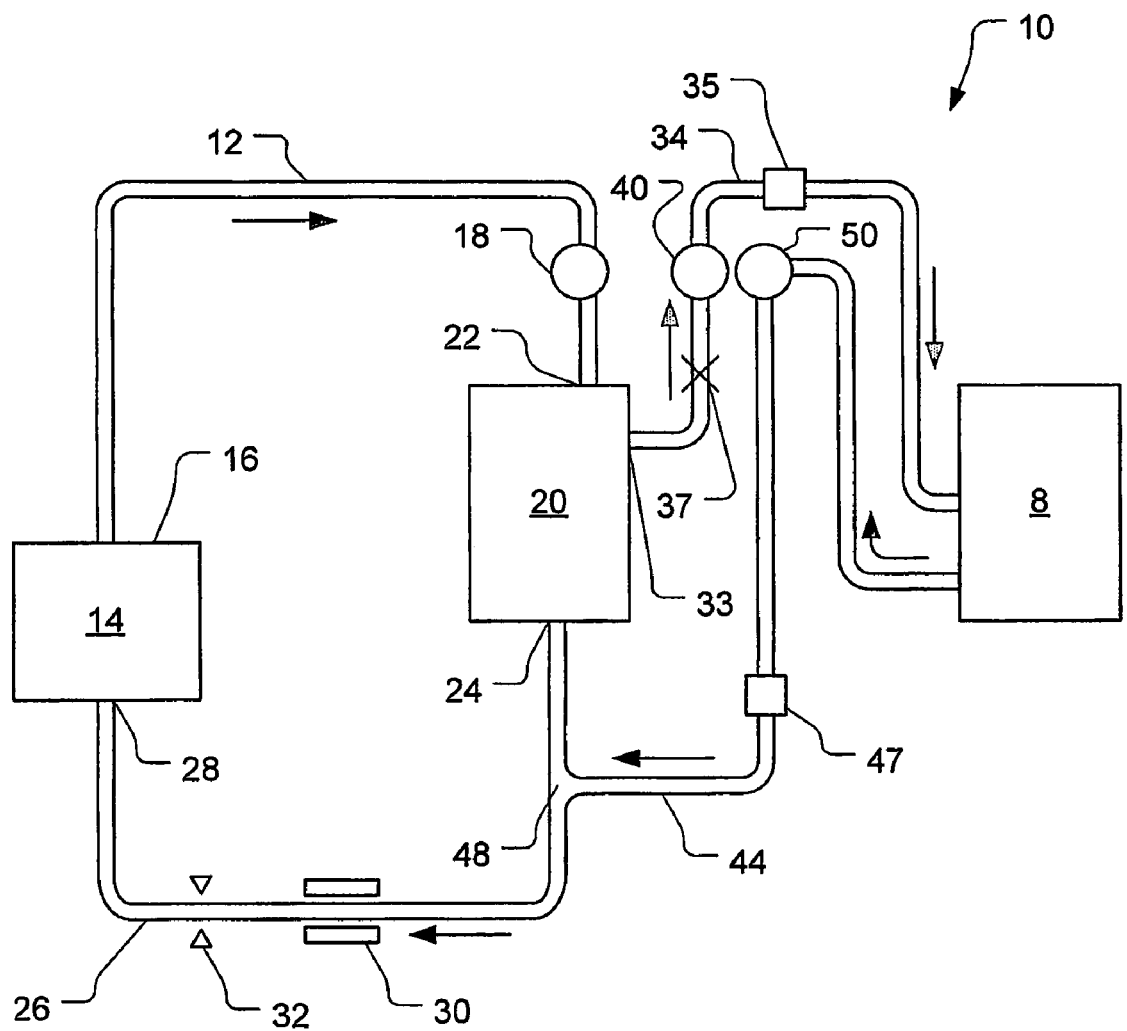
FIG. 10 is a schematic representation of a blood treatment system.

Waste balancing system 108 may be used as waste balancing system 8 in blood treatment system 10 depicted in FIG. 10. The arrangement of FIG. 10 facilitates a method for clearing a patient's blood of toxins by providing a protocol involving removing blood from the patient at a rate of at least 300 ml/min, at least partially clearing the blood of uremic toxins to create cleared blood, and returning the cleared blood to the patient. The protocol can be carried out at least four times per week. A patient blood withdrawal conduit 12 is connected to the vascular system of a patient 14 at a location 16 which, in preferred embodiments, is a high-flow rate valve port. Blood withdrawal conduit 12 is routed through a pump 18 and supplies blood to a blood treatment unit 20 via an inlet port 22. In preferred embodiments, blood treatment unit 20 is a hemofilter. Alternatively, blood treatment unit 20 may be a dialysis machine. Treated blood, from which waste product has been removed by blood treatment unit 20, exits blood treatment unit 20 at outlet 24 and is delivered, via conduit 26, to the vascular system of patient 14 preferably by way of location 28 which, in preferred embodiments, is a high-flow rate port. An ultrasonic detector 30 can be provided along conduit 26 between blood treatment unit 20 and patient 14 to detect any or all of flow rate, air bubbles (foam), and hematocrit. A safety clamp 32 can be provided as well to stop flow if detector 30 indicates the presence of unacceptable levels of air bubbles.

Waste product (waste filtrate in a hemofiltration system) exits blood treatment unit 20 via port 33 and passes through conduit 34 into waste balancing system 8. Conduit 34 passes through a pump 40. A blood detector 35 can be positioned along conduit 34 to detect any leaks in a filter within blood treatment unit 20. The detector detects red blood cells which, if a filter rupture has occurred, will leak into conduit 34, rather than being returned to patient 14. The detector can be controlled by a treatment controller, and operably and electronically linked to a system that stops treatment. An articulated clamp 37 can be positioned along conduit 34 to control, or at least fine tune, the rate of flow through pump 40.

Waste balancing system 8 is fluidly connected to conduit 26 via a replacement fluid conduit 44 with a connection 48 between conduit 44 and conduit 26. Conduit 44 passes through a pump 50. Waste balancing system 8 need include only that amount of infusate required for a particular treatment. Where a bi-daily (every other day) protocol is indicated, waste balancing system 8 may initially contain from about 8 to about 24 liters of infusate. Where a daily protocol is indicated, waste balancing system 8 may initially contain from about 8 to about 12 liters of infusate.

A sterile filter 47 is positioned in conduit 44 between pump 50 and conduit 26.

Pumps 18, 40, and 50 may be individual peristaltic pumps or combined as a single peristaltic pump, for example.

When waste balancing system 108 is used as waste balancing system 8 in FIG. 10, waste 170 may be delivered to flexible bag 160 by conduit 34 and replacement fluid 130 may be delivered from flexible bag 120 to patient 14 via conduit 44.

Alternatively, waste balancing system 8 may comprise a flow meter for measuring the amount of waste flowing through conduit 34. A controller may then control pump 50 to pump an amount of replacement fluid selected on the basis of the measured waste flow. For example, to operate in a balanced condition, the controller may control pump 50 to pump an amount of replacement fluid equal to the measured waste flow.

Figure 11:
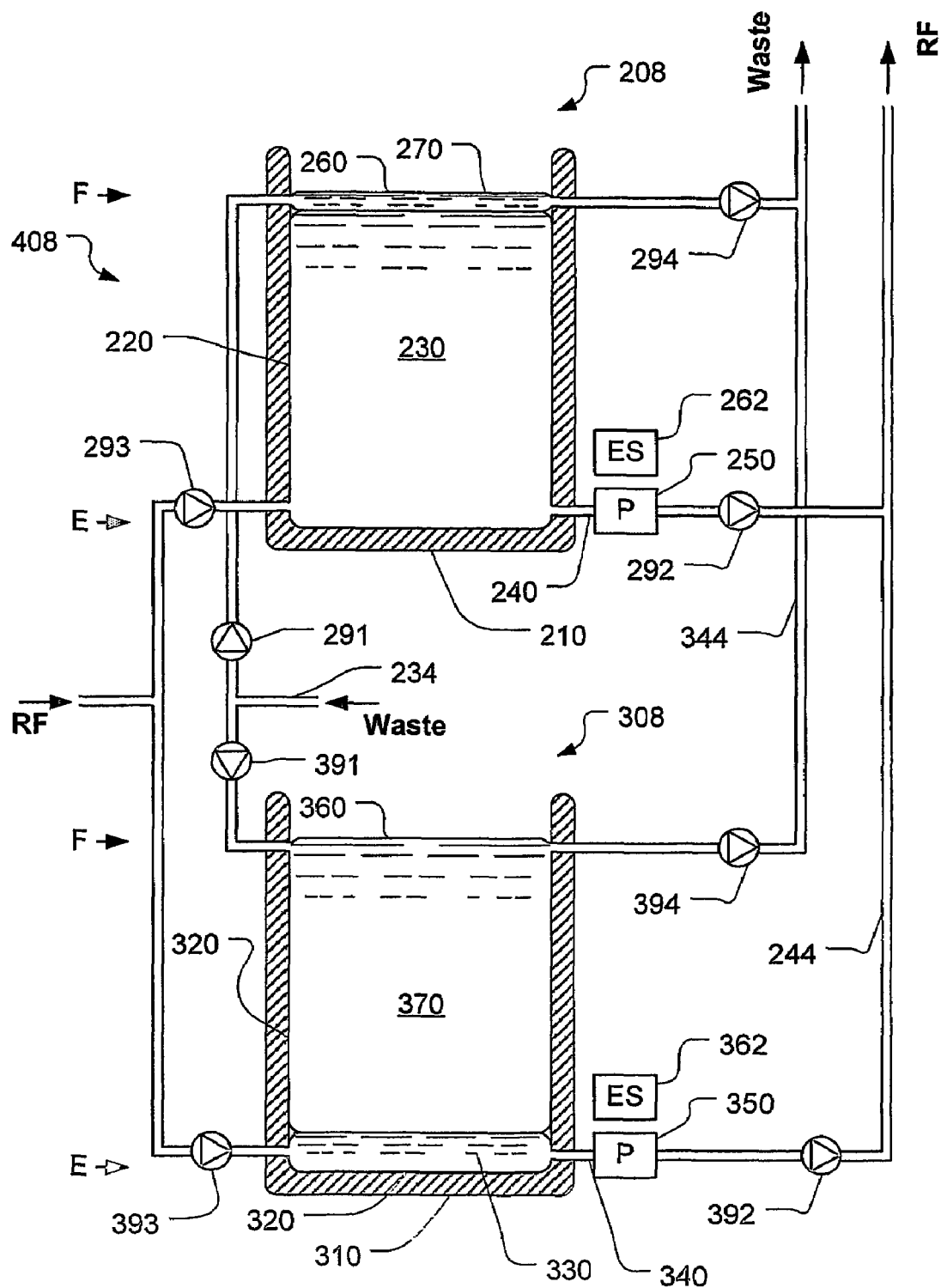
FIG. 11 is a diagrammatic depiction of a multiple balancing system.

FIG. 11 shows multiple balancing system 408. Multiple balancing system 408 has waste balancing system 208 and waste balancing system 308. Waste balancing system 208 and waste balancing system 308 may both be structurally identical to waste balancing system 108 depicted in FIG. 1 or waste balancing system 908 depicted in FIG. 13, for example. In multiple balancing system 408, one of the two waste balancing systems 208 and 308 may be functioning as described above in connection with FIGS. 2 through 4 while the other one is being restored to the initial state depicted in FIG. 1.

For example, FIG. 11 depicts waste balancing system 208 in its initial state, i.e., full of replacement fluid and containing no waste fluid. Waste balancing system 308 is shown in its final state, i.e., substantially empty of replacement fluid and full of waste fluid. These conditions may result from operating multiple balancing system 408 for one half of a complete cycle, as follows.

During the first half of a cycle, pumps 391 and 392 are activated, causing waste 370 from a patient to travel from waste line 234 into flexible bag 360. The pressure from the weight of waste 370 forces an equivalent weight of replacement fluid 330 to be released from flexible bag 320 through valve 340, as regulated by pressure element 350, and is pumped by pump 392 to a patient via replacement line 244. The first half of the cycle is complete when flexible bag 320 is depleted down to level E as detected by empty sensor 362, for example.

When the first half of the cycle is completed, pumps 391 and 392 are deactivated, and pumps 291, 292, 393, and 394 are activated, initiating the second half of the cycle. The activation of pumps 291 and 292 causes waste 270 from the patient to travel from waste line 234 into flexible bag 260. The pressure from the weight of waste 270 forces an equivalent weight of replacement fluid 230 to be released from flexible bag 220 through valve 240, as regulated by pressure element 250, and may be provided to a patient via replacement line 244. Activation of pump 393 causes replacement fluid 430 from replacement fluid source 420 to flow into flexible bag 320. Activation of pump 394 causes waste 370 that accumulated during the first half of the cycle in flexible bag 360 to be transported to waste dump 460. The depletion of flexible bag 220 down to level E may be detected by empty sensor 262, for example. The second half of the cycle is complete when flexible bag 220 is depleted down to level E, flexible bag 320 is fully replenished with replacement fluid 430, and flexible bag 360 is emptied of waste 370.

A new cycle begins with deactivation of pumps 291, 292, 393, and 394, and activation of pumps 391, 392, 293, and 294. The activation of these pumps returns waste balancing system 208 from a depleted state to the full state depicted in FIG. 11.

In the embodiment of FIG. 11, replacement fluid source 420 may be many times larger than flexible bags 220 and 320, and waste dump 460 may be many times larger than flexible bags 260 and 360. This permits waste balancing systems 208 and 308 to be compactly located together remote from replacement fluid source 420 and waste dump 460. In this case, waste balancing system 208 and waste balancing system 308 may be many times smaller than, but structurally similar to, waste balancing system 108 depicted in FIG. 1 or waste balancing system 908 depicted in FIG. 13, for example.

Alternatively, pressure elements 250 and 350 may be replaced by weight scales and a controller adapted to maintain a constant weight in containers 210 and 310 in multiple balancing system 408. In this case, the controller would control the system's pumps to pump replacement fluid in response to the weight of waste added to container 210 and 310.

Figure 14:
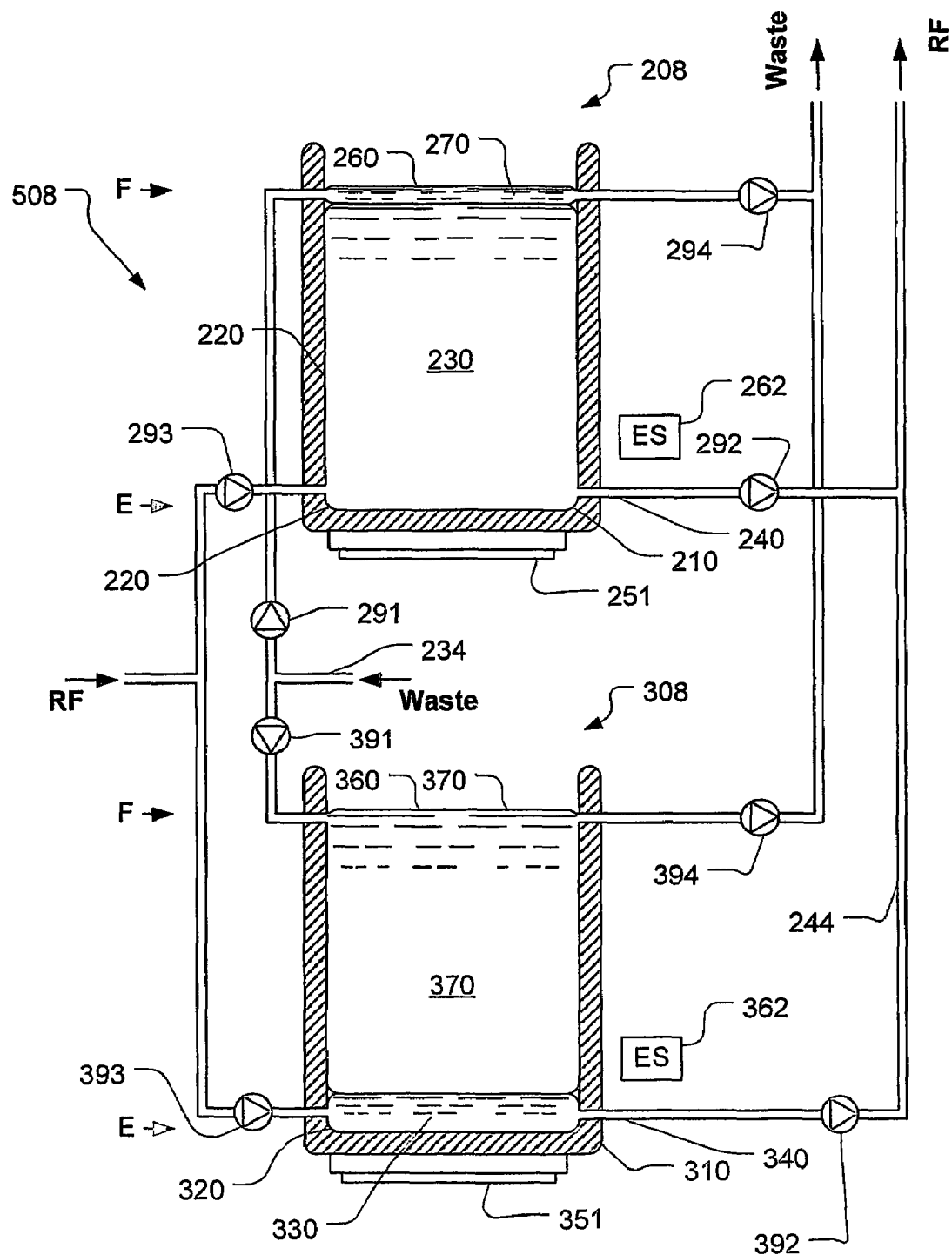
FIGS. 14, 15, 16, 17, and 18 are illustrations of alternative embodiments of multiple balancing systems.

FIG. 14 illustrates such a system. Multiple balancing system 508 employs scales 251 and 351 instead of pressure elements 250 and 350, respectively.

Alternatively, a system may employ both scales and pressure elements as redundant controls. When both the scales and the pressure elements are functioning as described above, the redundancy improves accuracy. This may be thought of as reducing the signal-to-noise ratio of the data used as evaluation characteristics. On the other hand, when one or more of the scales or pressure elements fails, the redundancy ensures continuous operation.

Figure 15:
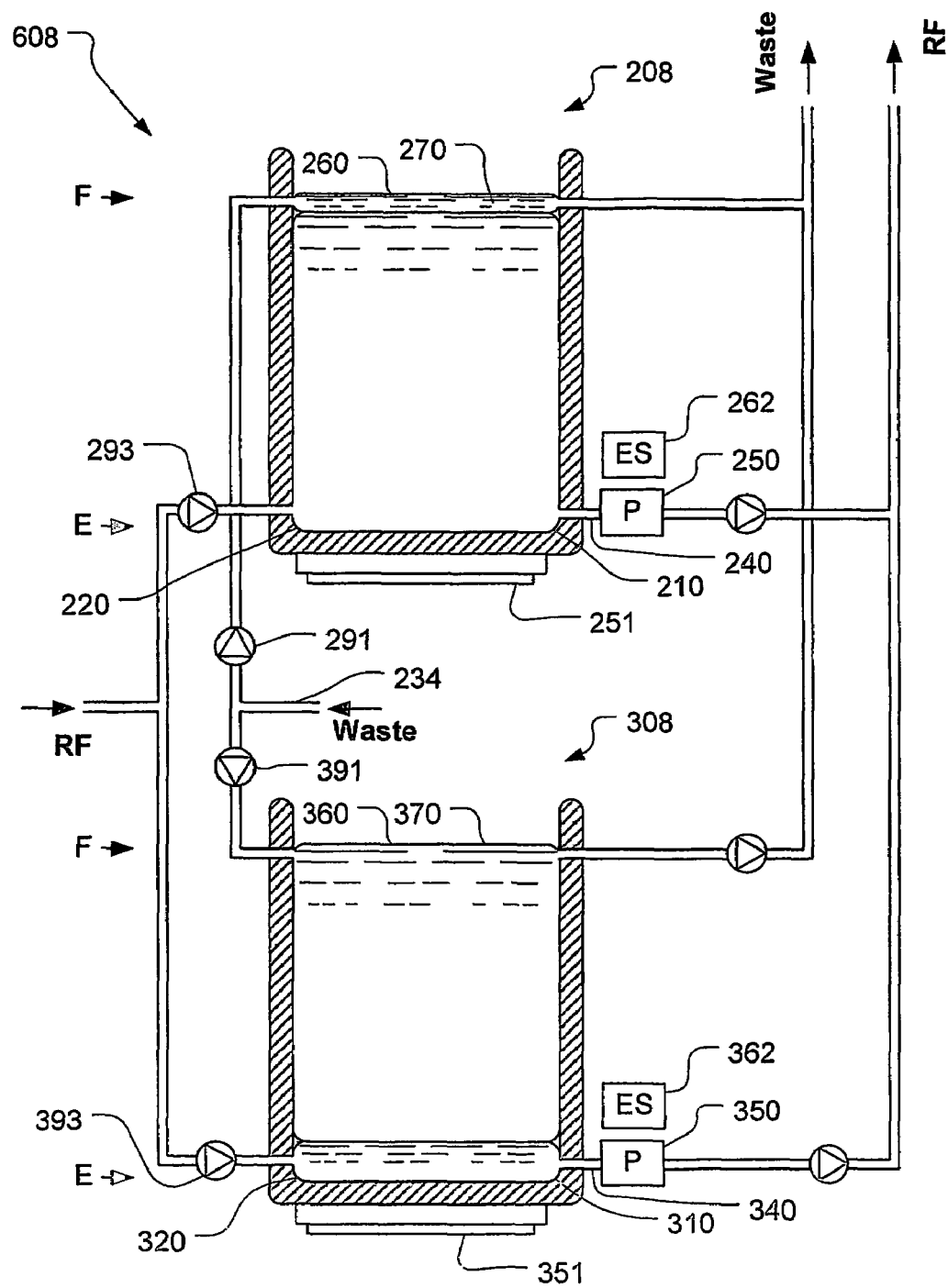

FIG. 15 illustrates an example of a redundant system. Redundant system 608 may normally operate in a selected one of the modes described above with respect to FIG. 11 and FIG. 14. If the selected mode encounters difficulty such as faulty equipment or an alarm condition, redundant system 608 may switch to another of the modes. For example, if redundant system 608 normally operates in the scale mode described in connection with FIG. 14 using a controller to determine the amount of replacement fluid to pump based on the measured weight of container 210, a problem with the controller may prevent proper operation of redundant system 608. In that event, redundant system may switch to the pressure element mode of operation described in connection with FIG. 11.

If redundant system 608 normally operates in the pressure element mode, for example, redundant system 608 may concurrently operate in the scale mode as a check on the accuracy of operation. If a discrepancy is detected, the system may automatically correct itself or signal an alarm condition.

When multiple balancing system 408 is used as waste balancing system 8 in FIG. 10, waste may be delivered to waste line 234 by conduit 34, and replacement fluid may be delivered from replacement fluid line 244 to conduit 44.

Figure 12:
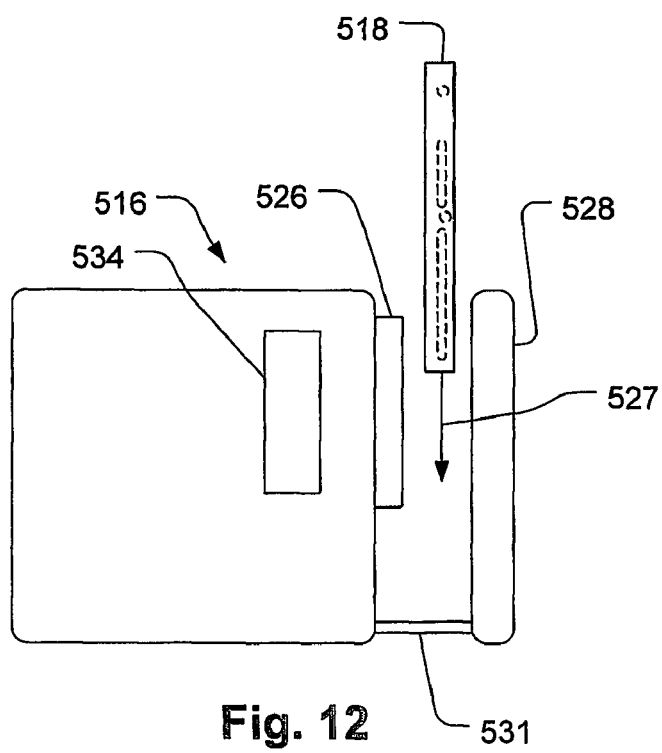
FIG. 12 is a side elevational drawing of a hemofiltration machine.

FIG. 12 shows hemofiltration machine 516. Hemofiltration machine 516 may employ multiple balancing system 408 to replace waste, removed from a patient by hemofilter 534, with replacement fluid. Hemofilter 534 may form an integrated part of disposable cartridge 518, if desired. The elements of multiple balancing system 408 may be distributed in hemofiltration machine 516 as follows, for example. Flexible bags 220, 260, 320, and 360 may be contained in disposable cartridge 518 in slot 527. Indentations (not shown) on chassis panel 526 register with comparable indentations (also not shown) on door 528 when door 528 is slid along rails 531 to sandwich cartridge 518 between door 528 and chassis panel 526. Upon registration, these indentations may combine to form containers 210 and 310. The remaining elements of multiple balancing system 408 as described in connection with FIG. 11 may be contained within hemofiltration machine 516. Alternatively, replacement fluid source 420 and/or waste dump 460 may be situated external to hemofiltration machine 516 with appropriate connections to pumps 292, 293, 393, and 394 within hemofiltration machine 516.

Flexible bags 120, 160, 220, 260, 320, and 360 as described are expandable containers. Any or all of these may be replaced with other expandable containers. For example, such an expandable container may comprise accordion or flexible sides with a rigid top and bottom. Or, an expandable container may comprise a flexible elastic bag. Alternatively, instead of using an expandable container, some or all of flexible bag pairs 120/160, 220/260, and 320/360 may be replaced with a piston or other partition in sealed moveable engagement with the sides of container 110, 210, or 310.

Figure 13:
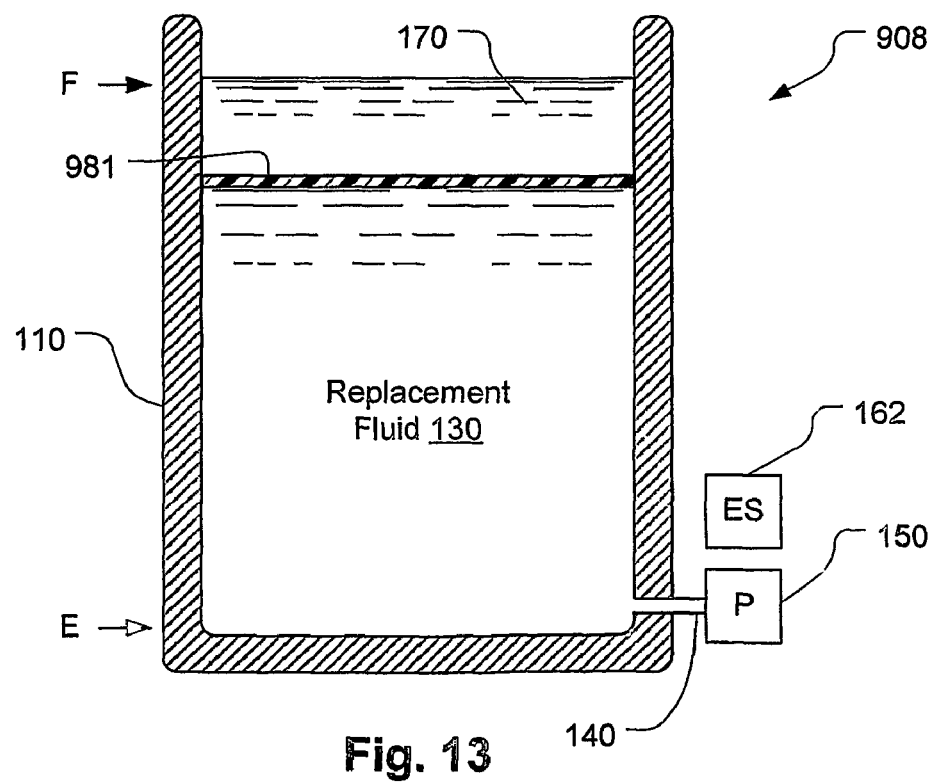
FIG. 13 is a diagrammatic depiction of a waste balancing system.

FIG. 13 depicts waste balancing system 908. Waste balancing system 908 operates similarly to waste balancing system 108 but flexible bag pair 120/160 has been replaced with piston 981 in sealed moveable engagement with the sides of container 110. As waste 170 is added on top of piston 981, piston 981 can move down in order to push replacement fluid 130 out of container 110 through valve 140. This movement may be sensed and/or controlled by pressure element 150. The amount of replacement fluid 130 that exits container 110 below piston 981 through valve 140 may be balanced against the amount of waste added above piston 981 in container 110. For example, pressure element 150 may sense and/or control the passage of replacement fluid 130 through valve 140 in like manner describe above. Pressure element 150 may maintain a constant fluid pressure at valve 140 or a constant level of the combined height or weight of waste 170 and replacement fluid 130.

In any of the embodiments described herein, a waste balancing system may be operable to achieve balance, ultrafiltration, and/or bolus conditions. In a balance condition, the amount of replacement fluid leaving a waste balancing system is approximately equal to the amount of waste entering a waste balancing system. This may be indicated when a patient is to receive replacement fluid in an amount approximately equal to the amount of waste removed from the patient's blood stream. In an ultra-filtration condition, the amount of replacement fluid leaving a waste balancing system is less than the amount of waste entering a waste balancing system. This may be indicated when a patient is to receive replacement fluid in an amount less than the amount of waste removed from the patient's blood stream. In a bolus condition, the amount of replacement fluid leaving a waste balancing system is greater than the amount of waste entering a waste balancing system. This may be indicated when a patient is to receive replacement fluid in an amount greater than the amount of waste removed from the patient's blood stream.

Any given waste balancing system disclosed herein may be automatically or manually adjustable before or during operation to achieve one or more of the balance, ultrafiltration, and bolus conditions. For example, the extent of ultrafiltration may be adjusted to achieve a desired amount of net fluid loss for a patient. Pressure element 150 may be set to maintain the combined fluid level in container 110 at a fixed or increasing level higher than F. As another example, some percentage or absolute amount of the waste entering waste balancing system 108 may be siphoned off without being added to container 110. Waste may be siphoned off before reaching waste balancing system 8.

FIG. 14 depicts multiple balancing system 508. Multiple balancing system 508 is comparable to multiple balancing system 408 depicted in FIG. 11, except that sensing functions of pressure elements 250 and 350 are performed by scales 251 and 351, respectively. Scale 251 weighs container 210 in order to detect the change in weight caused by waste 234 entering flexible bag 270. This information is provided to an operator (not shown). The operator may be an electronic controller, an attendant, a remote medical professional, or the patient, for example. The operator uses the information as an evaluation characteristic and determines therefrom a control parameter for operation of pump 292. For example, if it is desired to operate multiple balancing system 508 in a balanced condition and waste removed from a patient is added to flexible bag 260 in container 210, the operator may determine that pump 292 should be operated so as to cause replacement fluid 230 to be pumped out of container 210 and provided to a patient via conduit 244 in an amount required to maintain container 210 at a constant total weight. The operator may use a flow rate associated with pump 292 as a control parameter. Or, the operator may simply use an on/off control for pump 292 as a control parameter, controlling pump 292 to be on until such time as scale 251 indicates to the operator that the weight of container 210 has been maintained. Thus, the patient may be provided replacement fluid in an amount (mass) equal to the mass of the removed waste.

Waste balancing system 308 may be operated in similar fashion in a cycle alternating with waste balancing system 208 as described in connection with FIG. 11 in order to provide the patient uninterrupted availability or constant flow of replacement fluid from multiple balancing system 508. A third waste balancing system (not shown) may be available to switch in as a backup in case waste balancing system 208 or waste balancing system 308 becomes unavailable or inoperable. Thus, uninterrupted availability of replacement fluid may be assured even if a waste balancing system in multiple balancing system 508 is out of service.

As shown in FIG. 14, multiple balancing system 508 may be implemented as a tandem waste balancing system without a third waste balancing system.

FIG. 15 illustrates multiple balancing system 608. Multiple balancing system 608 is similar to multiple balancing system 508 but employs both pressure element 250 and scale 251. For example, pressure element 250 may provide redundancy as a back-up to or accuracy check on the operations described in connection with scale 251.

Figure 16:
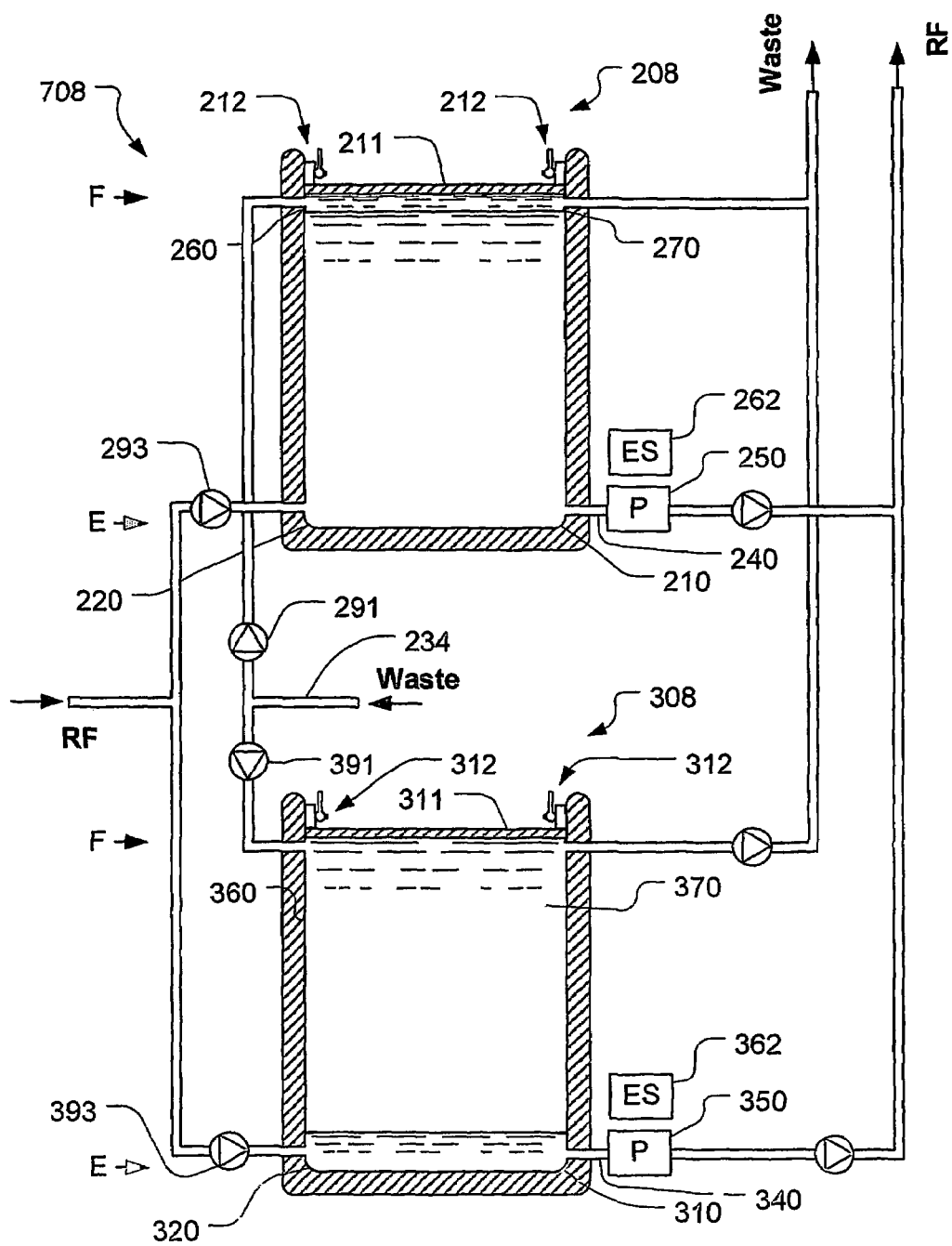

FIG. 16 illustrates multiple balancing system 708. Multiple balancing system 708 is comparable to multiple balancing system 408 described in connection with FIG. 11, except for the addition of cap 211 (and cap 311). Cap 211 is fixed at a certain height in container 210. For example, cap 211 may be installed at a selected height F by clamping cap 211 to container 210 with clamps 212. Once installed in place, cap 211 defines and fixes a certain maximum volume below cap 211 in container 210. This maximum volume serves as an upper limit on the combined volume of flexible bags 260 and 220. During operation of waste balancing system 208, when the combined volume of flexible bags 260 and 220 equals the maximum volume, no more waste can be added to flexible bag 260 unless an equal or greater volume of replacement fluid exits flexible bag 220. Pressure element 250 and empty sensor 262 may be included for redundancy.

Waste balancing system 208 as shown in FIG. 16 may be initially set up as follows. First, flexible bag 220 is established in its full condition in container 210. Second, flexible bag 270 is established in its empty condition on top of and in contact with flexible bag 220 in container 210. Third, cap 211 is placed on top of and in planar contact with flexible bag 270. Fourth, cap 211 is fixed in place with clamps 212.

After waste balancing system 208 is set up as shown in FIG. 16, it may operate to balance waste against replacement fluid based on both volume and mass. Cap 211 may provide a volume-based evaluation characteristic and control parameter, and pressure element 250 may concurrently or alternatively provide a mass-based evaluation characteristic and control parameter.

Figure 17:
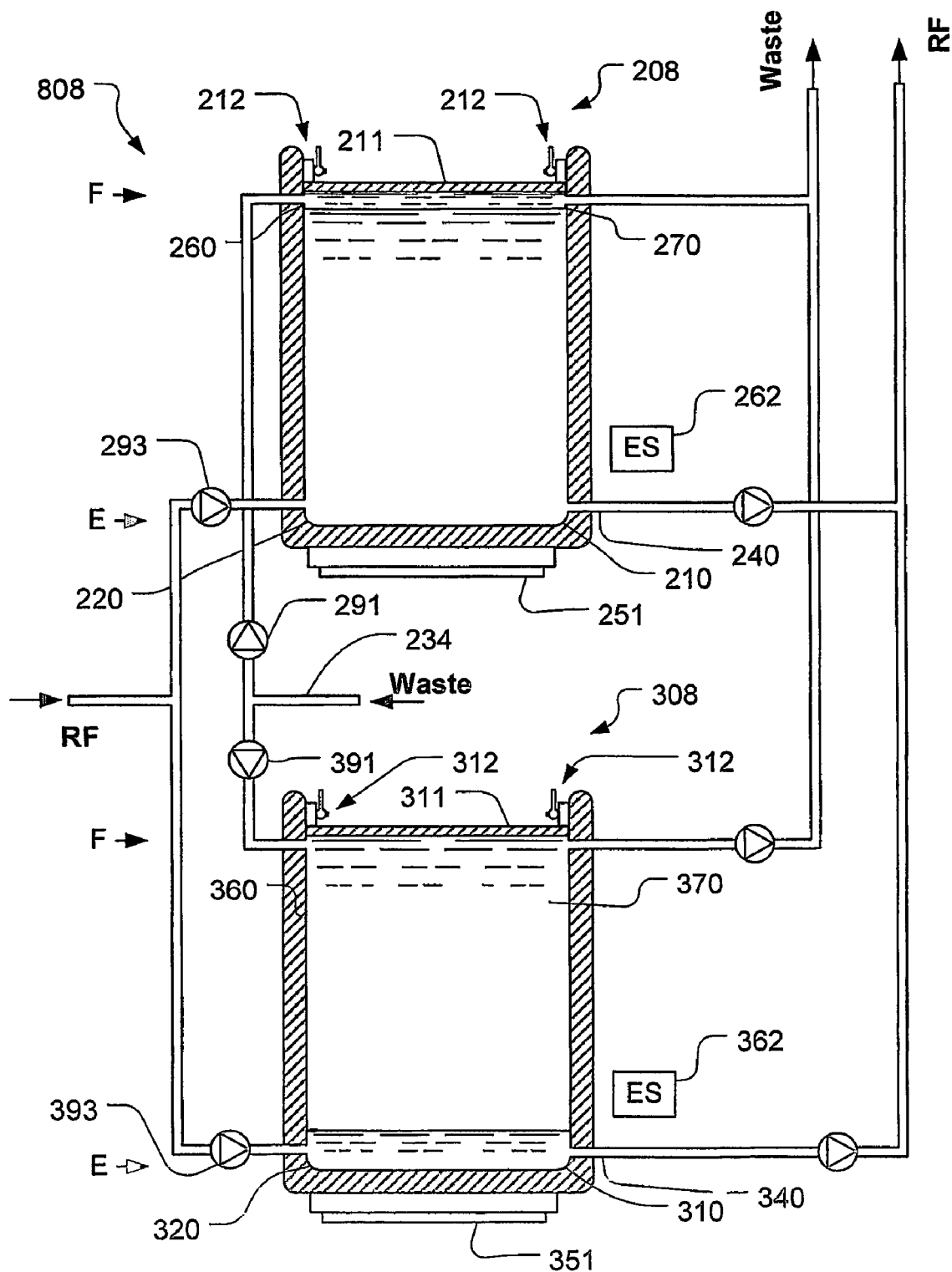

FIG. 17 illustrates multiple balancing system 808. Multiple balancing system 808 is similar to multiple balancing system 708 except that pressure element 250 has been removed and scale 251 has been added. Additionally, cap 211 may be permanently pre-installed at level F, creating a permanent fixed-volume chamber within container 210 below cap 211. In operation, the fixed-volume chamber provides a mechanical volume-based evaluation criteria by sensing the volume of waste fluid received and also provides a mechanical volume-based control parameter by controlling the volume of replacement fluid provided to the patient. Scale 251 may provide the weight of container 210 as a secondary evaluation characteristic. During operation, if the secondary evaluation characteristic indicates a value outside of a pre-determined range or percentage variation, an alarm condition may be generated.

For example, if the secondary evaluation characteristic indicates that the weight of container 210 has risen higher than an upper bound, an alarm condition may cause pump 291 to be deactivated. Or, if the secondary evaluation characteristic indicates that the weight of container 210 has fallen lower than a lower bound, an alarm condition may cause pump 292 to be deactivated.

Waste balancing system 308 may operate in a cycle opposite that of waste balancing system 208 in multiple balancing system 808.

Figure 18:
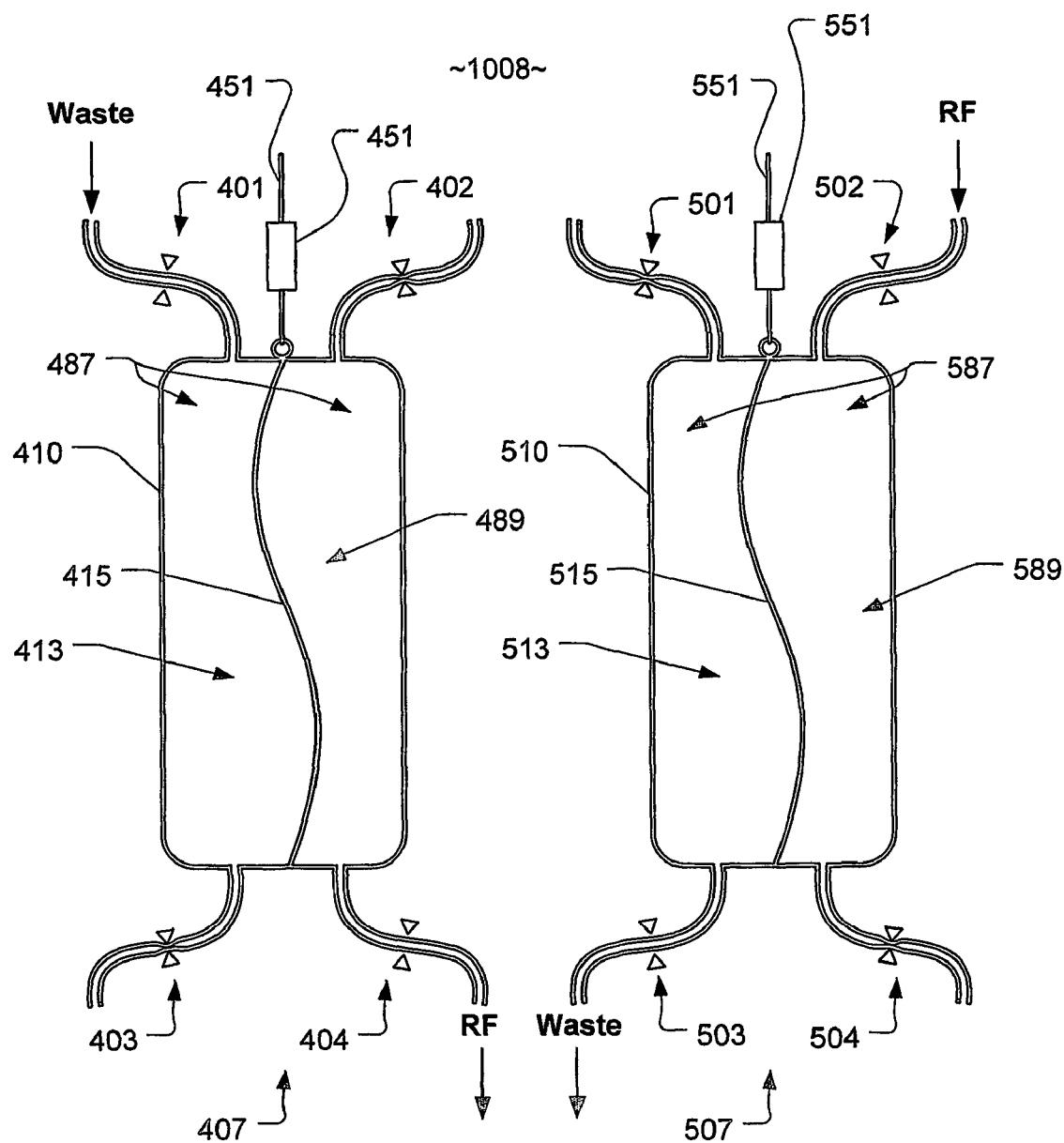

FIG. 18 represents multiple balancing system 1008. Multiple balancing system 1008 is shown having identical containers 410 and 510. Container 410 defines a chamber 487 having a permanently fixed volume and comprising waste compartment 413 and replacement fluid compartment 489 divided by divider 415. Divider 415 may be a diaphragm, for example. Alternatively, waste compartment 413 and replacement fluid compartment 489 may each comprise a flexible plastic bag inside of chamber 487, with divider 415 being formed by fusing together the contacting portions of the two flexible plastic bags. Scale 451 reflects the combined weight of the contents of waste compartment 413 and replacement fluid compartment 489.

In the state shown in FIG. 18, container 410 has a waste-fluid-in valve open, permitting waste fluid to flow into waste compartment 413. A replacement-fluid-out valve is also open, permitting replacement fluid to flow out of replacement fluid compartment 489. When chamber 487 is full, the addition of a volume of waste fluid to waste compartment 413 forces an equal volume of replacement fluid to exit replacement fluid compartment 489.

At the same time, container 510 is shown operating in a cycle opposite that of container 410. A waste-fluid-out valve is open, permitting waste fluid to flow out of waste compartment 513. A replacement-fluid-in valve is also open, permitting replacement fluid to flow into replacement fluid compartment 589. When chamber 587 is full, the addition of a volume of replacement fluid to replacement fluid compartment 589 forces an equal volume of waste fluid to exit waste compartment 513. In this manner, container 510 may be reset while container 410 is used to provide replacement fluid to a patient in need thereof. When waste compartment 413 becomes full or replacement fluid compartment 489 becomes empty, the cycle can be reversed, i.e., container 510 can provide replacement fluid to a patient while container 410 is reset.

While container 410 is providing replacement fluid to a patient or accepting waste fluid from a patient, scale 451 provides an additional margin of safety and reliability by reflecting the combined weight of the contents of waste compartment 413 and replacement fluid compartment 489. If the combined weight falls above or below a safety margin, an alarm condition may be indicated. As one possible result of such an alarm condition, the waste-fluid-in valve and replacement-fluid out valve of container 410 may be closed. Another possible result would be that only one of those two valves may be closed. For example, if the combined weight falls above a safety margin, the alarm condition may result in closing the waste-fluid-in valve while leaving open the replacement-fluid-out valve of container 410 until the combined weight is again within the safety margin.

Thus, fixed-volume chamber 487 makes available a volume-based evaluation characteristic and a volume-based control parameter. Scale 451 makes available a mass-based evaluation characteristic. Operation of the valves as described herein makes available a replacement flow on/off control parameter. A volume-based evaluation characteristic may be combined with a mass-based evaluation characteristic to determine appropriate values for control parameters to provide a desired amount of replacement fluid to a patient.

Figure 19:
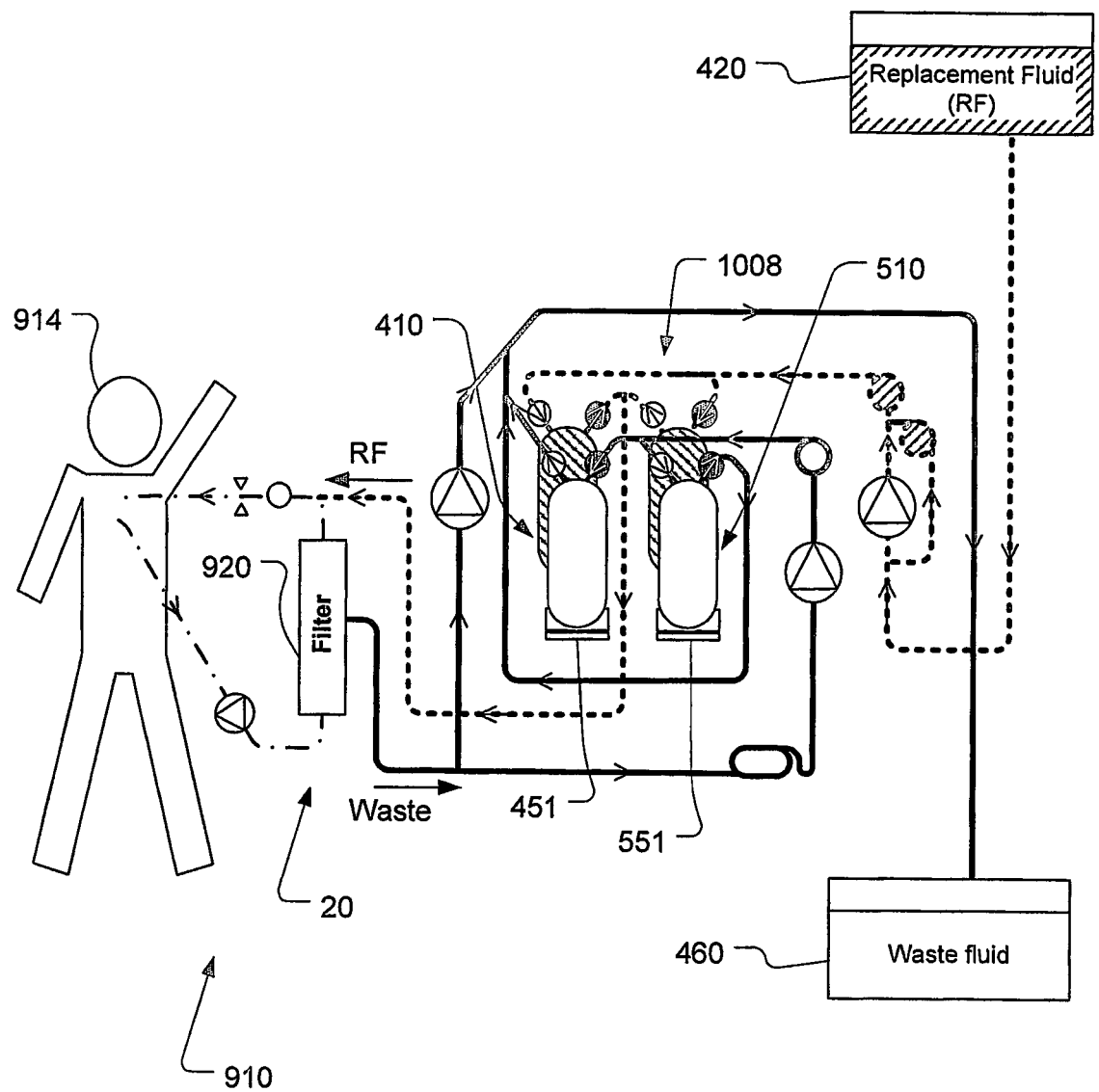
FIGS. 19, 20, 21, 22, 23, 24, 25, 26 and 27 are diagrammatic depictions of fluid circulating systems with alternative waste balancing systems.

FIG. 19 exemplifies implementation of multiple balancing system 1008 in a blood treatment system 910. Blood treatment system 910 treats the blood of patient 914 with blood treatment unit 20. As illustrated in FIG. 19, blood treatment unit 20 may be a hemofilter 920.

Figure 20:
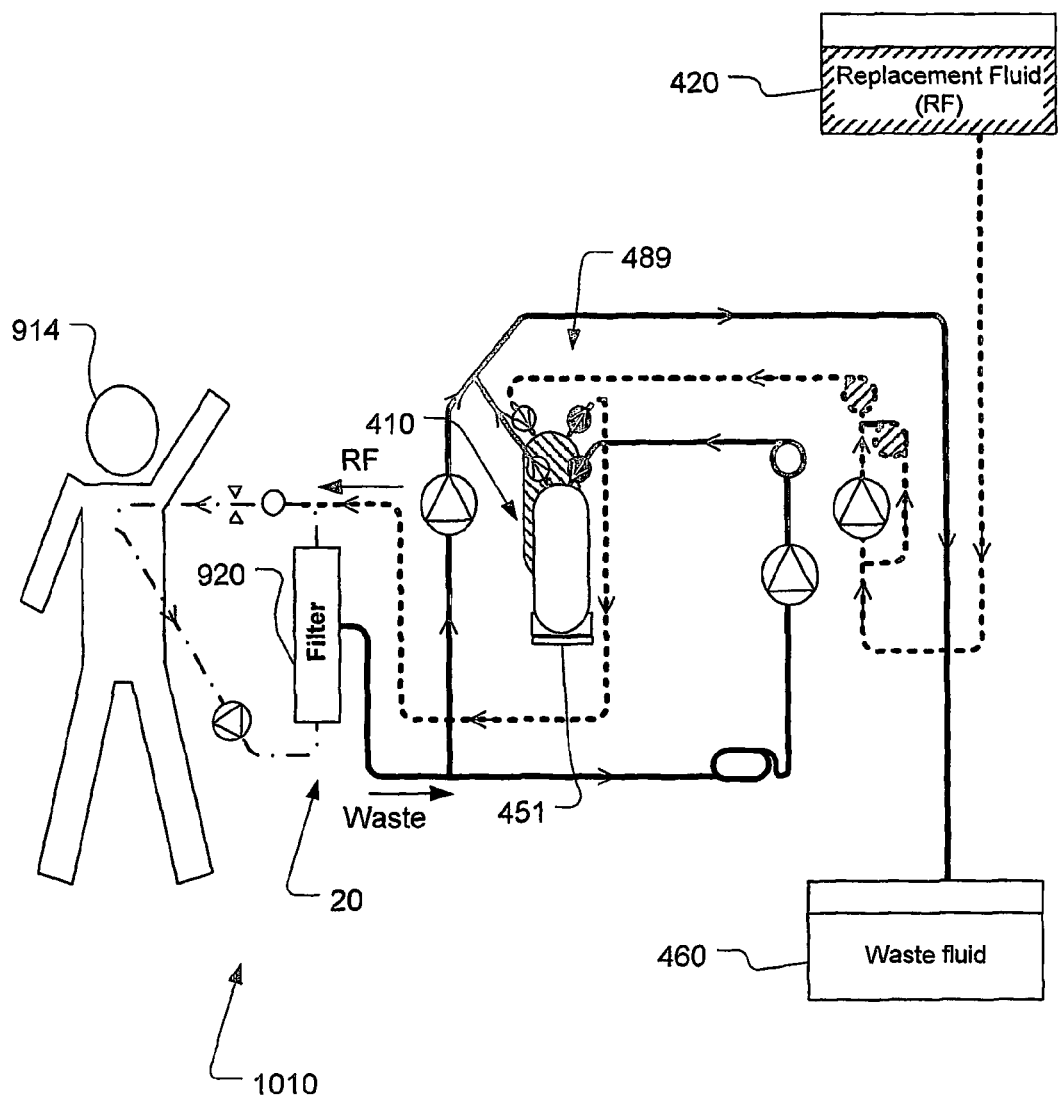

FIG. 20 is similar to FIG. 19 except that FIG. 20 only has one container 410. While chamber 487 is being reset as described above, replacement fluid could be temporarily halted or it could be provided directly from replacement fluid source 420. If replacement fluid is temporarily halted, blood treatment system 910 may continue to operate but in an ultrafiltration condition.

Figure 21:
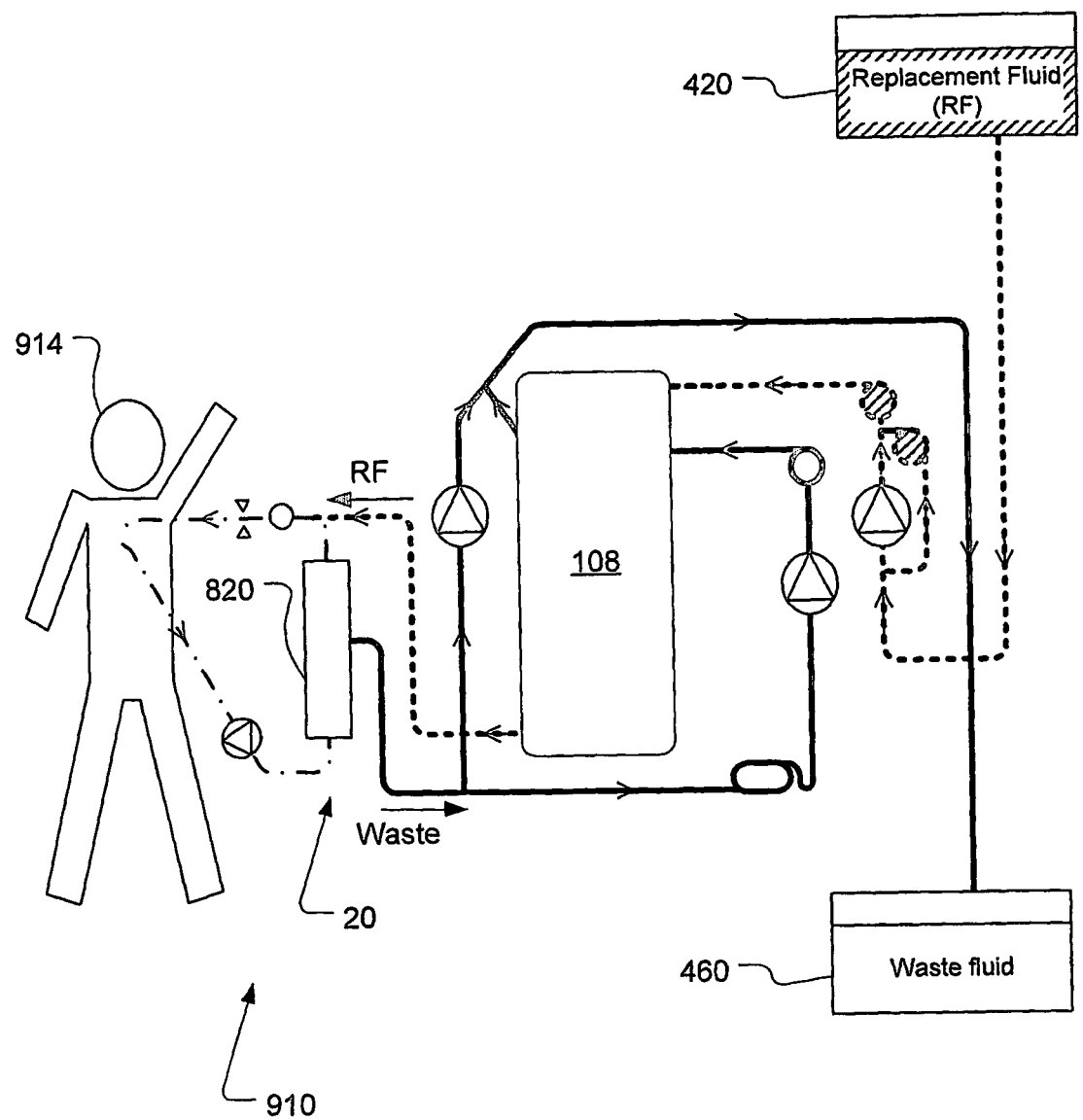

FIG. 21 illustrates implementation of waste balancing system 108 in blood treatment unit 20. Blood treatment unit 20 may for example be dialysis machine 820.

Figure 22A:
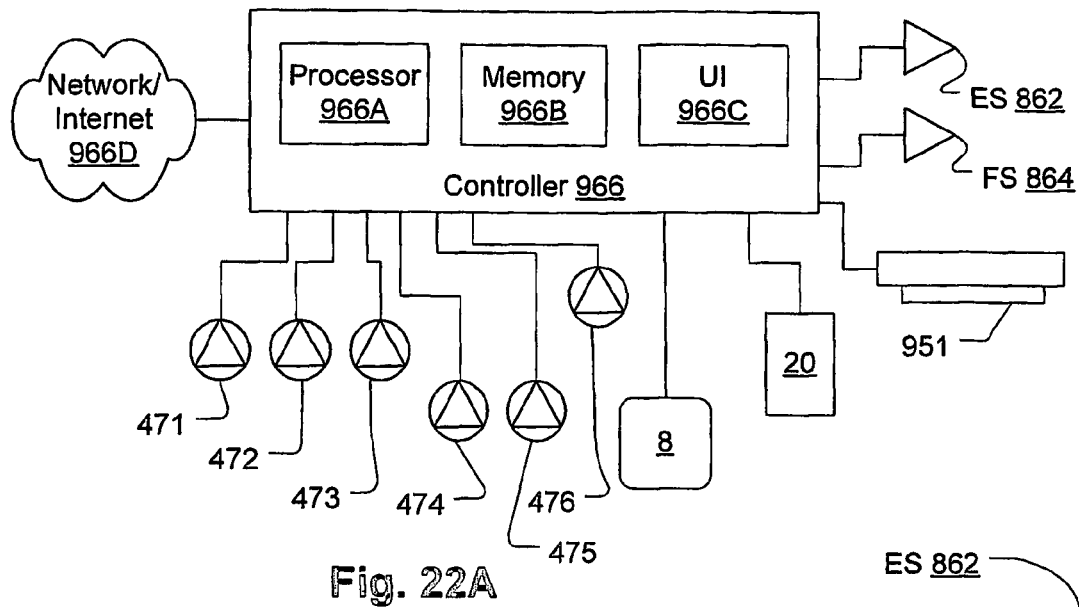
Figure 22B:
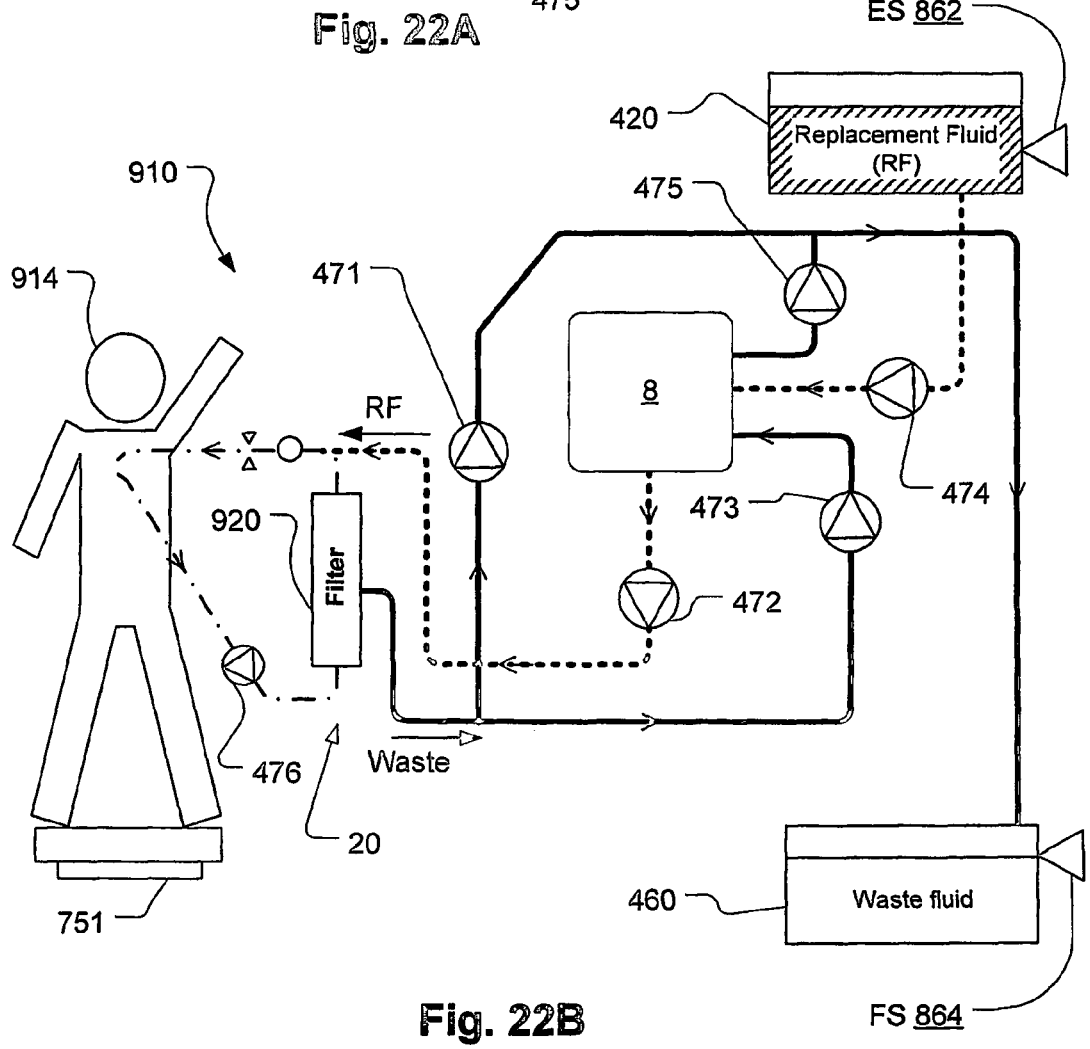

FIG. 22 shows blood treatment system 910 combined with waste balancing system 8, patient scale 951, and controller 966. Controller 966 may detect all available evaluation characteristics and control all available control parameters. For example, patient scale 951 may provide controller 966 with the patient's weight as an evaluation characteristic. Patient 914 may be weighed on patient scale 951, intermittently or continuously, during operation of blood treatment system 910.

The memory of controller 966 may store an ideal weight for patient 914. Alternatively, the processor of controller 966 may calculate an ideal weight by averaging previous measurements of the weight of patient 914 as detected by scale 951 and stored in the memory of controller 966. Or, controller 966 may determine the ideal weight by subtracting a desire ultrafiltration amount (or adding a desired bolus amount) to the weight of patient 914 at the beginning of treatment as detected by patient scale 951.

Controller 966 may operate the pumps in blood treatment system 910 or waste balancing system 8 to provide an amount of replacement fluid to patient 914 necessary to maintain or achieve the ideal weight. For example, during treatment of patient 914 by blood treatment system 910, if patient scale 951 detects a weight that exceeds the ideal weight for patient 914 by more than a threshold amount, controller 966 may activate the ultrafiltration pump to remove waste fluid from blood treatment unit 20 without providing a corresponding amount of replacement fluid to patient 914, until scale 951 indicates that patient 914 is at an acceptable weight. An acceptable weight may be a weight at or below the ideal weight, for example.

Patient hydration sensor 959 senses the hydration level of patient 914. For example, patient hydration sensor 949 may sense the density, color, and/or composition of blood removed from patient 914. The patient hydration level may approximate the level of hydration (or dehydration) of patient 914 as a percentage of the patient's body mass that is liquid, for example. The patient hydration level is made available to controller 966 as an evaluation characteristic and may supplement or supplant data from scale 951. For example, controller 966 may control the illustrated pumps to provide enough replacement fluid to maintain or achieve an acceptable hydration level stored in memory of controller 966 for patient 914.

Replacement fluid source 420 may have an empty sensor 862 to indicate an alarm condition to controller 966. Controller 966 may then make a connection over the Internet to order delivery of more replacement fluid, for example. Similarly, waste dump 460 may have full sensor 864 to indicate an alarm condition to controller 966. Controller 966 may then make a connection over the Internet to request emptying of waste dump 460, for example.

Figure 23A:
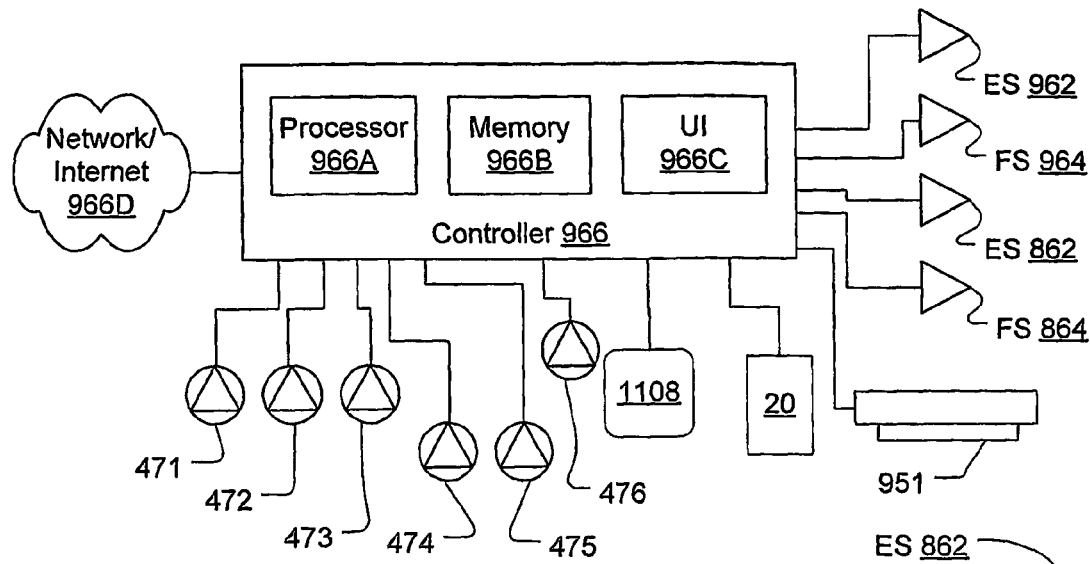
Figure 23B:
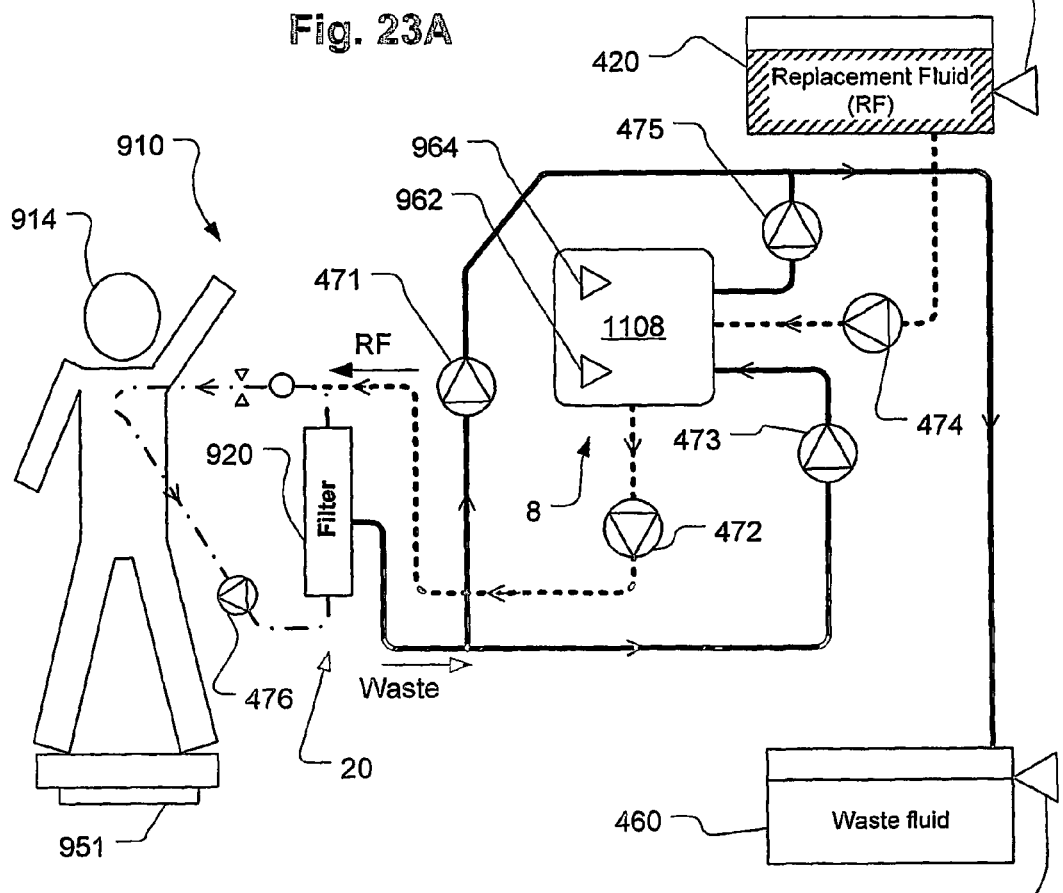

FIG. 23 shows waste balancing system 1108 implemented as the waste balancing system 8 of FIG. 22. Waste balancing system 1108 comprises flexible bag 160, flexible bag 120, full sensor 964, and empty sensor 962. Full sensor 964 is operable to detect when flexible bag 120 is full of replacement fluid. Empty sensor 962 is operable to detect when flexible bag 120 is empty. Full sensor 964 and empty sensor 962 provide input to controller 966, which in turn operates the pumps shown. Controller 966 may control balancing system 1108 to provide replacement fluid to patient 914 until empty sensor 962 detects that flexible bag 120 is empty. At that point, controller 96 may control the pumps to reset balancing system 1108 by emptying waste from flexible bag 160 to waste dump 460 and refilling flexible bag 120 with replacement fluid from replacement fluid source 420.

Figure 24A:
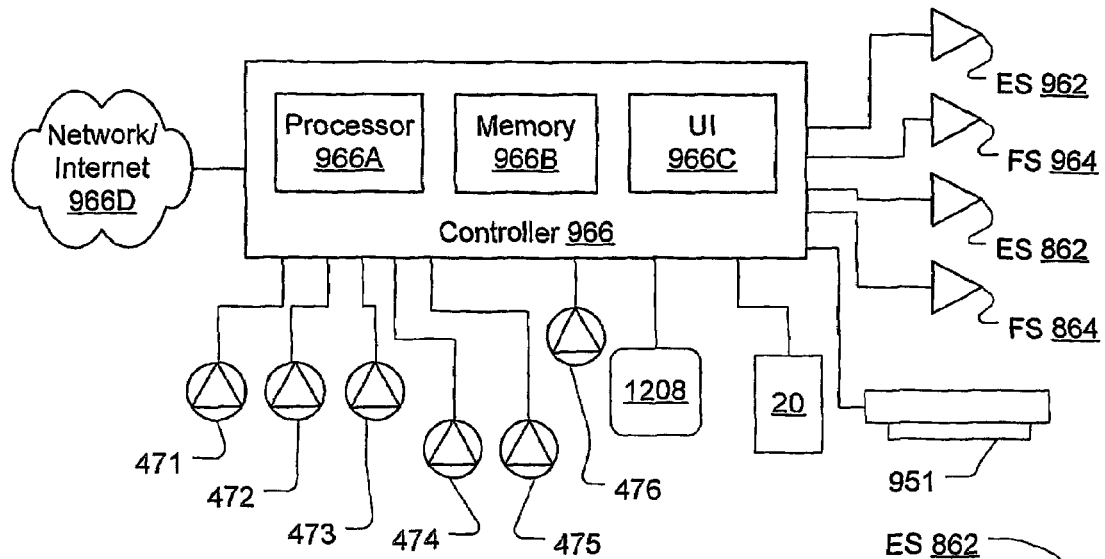
Figure 24B:
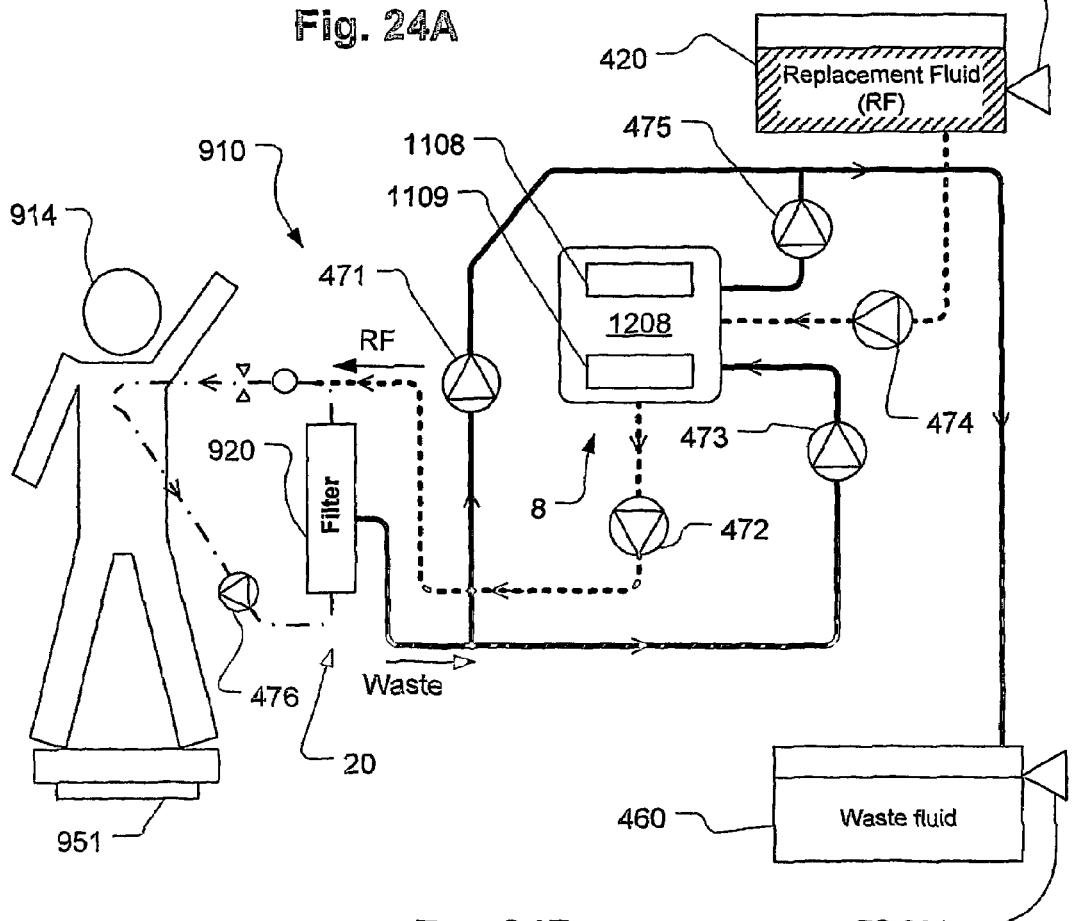

FIG. 24 is similar to FIG. 23 except that multiple balancing system 1208 comprises more than one waste balancing system. For example, multiple balancing system 1208 may consist of two or three waste balancing systems 1108, 1109, and so forth. In this embodiment, when balancing system 1108 is being reset, balancing system 1109 may be operated to supply replacement fluid to patient 914 and receive waste fluid from blood treatment unit 20 to permit continuous operation of multiple balancing system 1208.

Figure 25A:
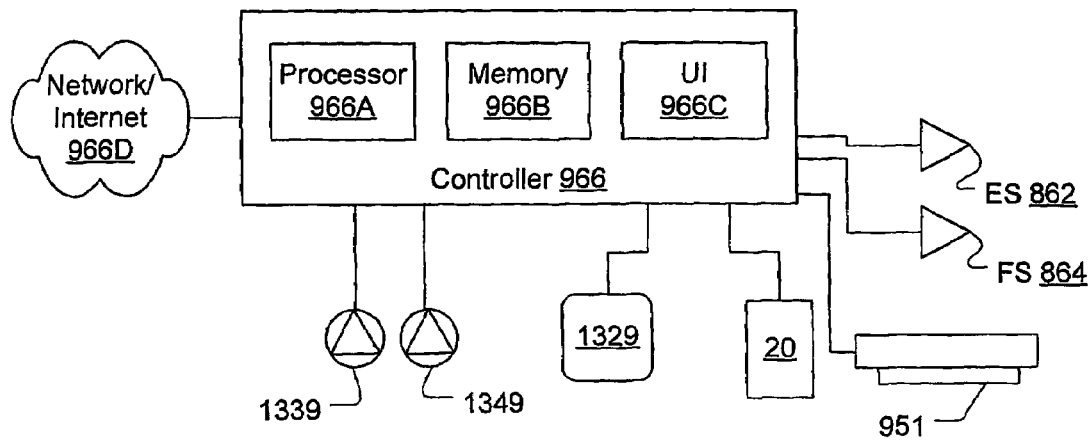
Figure 25B:
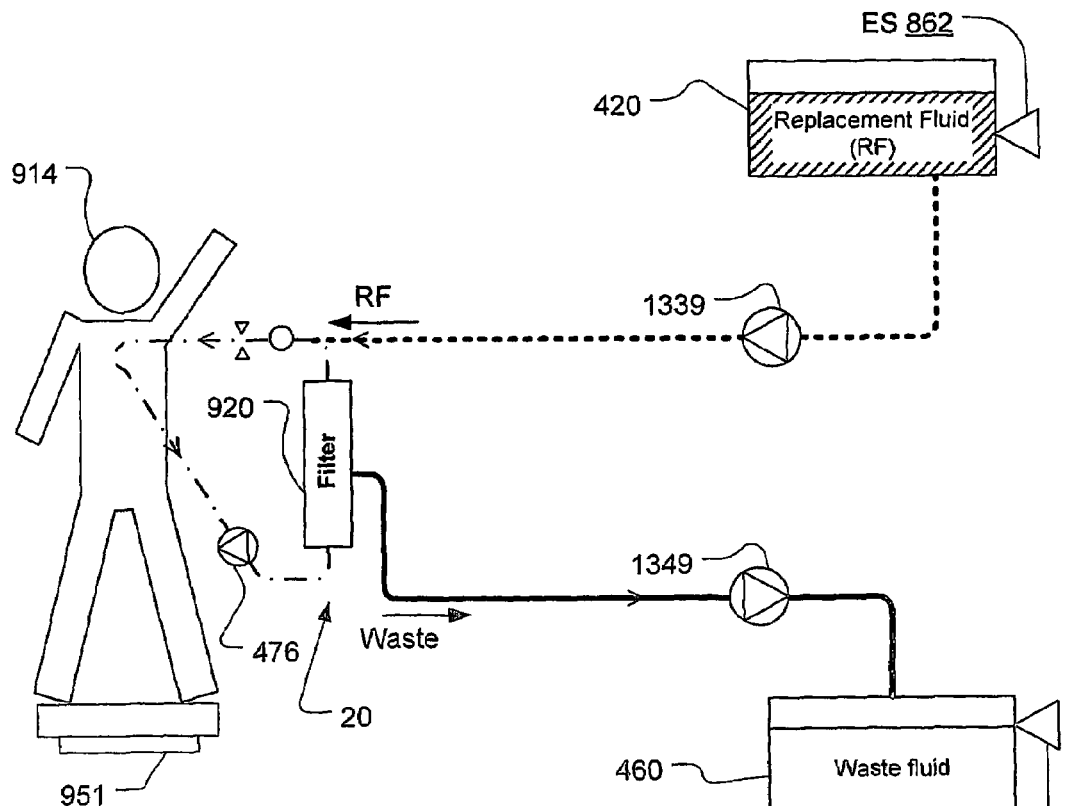

FIG. 25 illustrates implementation of waste balancing system 1308. Waste balancing system 1308 comprises a flow meter 1329 to measure waste removed from patient 914 and an RF pump 1339 to pump replacement fluid from replacement fluid source 420 to patient 914.

The output of flow meter 1329 may be provided to controller 966, which in turn controls RF pump 1339 to provide an appropriate amount of replacement fluid to patient 914. For example, for a balanced condition, controller 966 may control RF pump 1339 to pump an amount of replacement fluid equal to the amount of removed waste detected by flow meter 1329. For an ultrafiltration condition, controller 966 may control RF pump 1339 to pump an amount of replacement fluid less than the amount of removed waste detected by flow meter 1329. For a bolus condition, controller 966 may control RF pump 1339 to pump an amount of replacement fluid greater than the amount of removed waste detected by flow meter 1329.

Flow meter 1329 may use a strain gauge or laser Doppler to measure viscous flow, for example. Flow meter 1329 may use vortex shedding, orifice or nozzle pressure drop, or Pitot tube to measure turbulent flow, for example. Controller 966 may integrate over time a changing flow velocity detected by flow meter 1329 in order to determine the total amount of waste removed from patient 914 via blood treatment system 20 and waste pump 1349.

Flow meter 1329 may be of a type that is less accurate at flow amounts below a minimum threshold. In that case, controller 966 controls waste pump 1349 to pump only when flow meter 1329 detects a flow amount greater than the minimum threshold. A buffer (not shown) between blood treatment unit 26 and flow meter 1329 may accumulate waste when waste pump 1349 is deactivated. A level sensor (not shown) in the buffer may indicate to controller 966 when the buffer has accumulated enough waste to ensure a flow amount greater than the minimum threshold, causing controller 966 to restart waste pump 1349.

Figure 26:
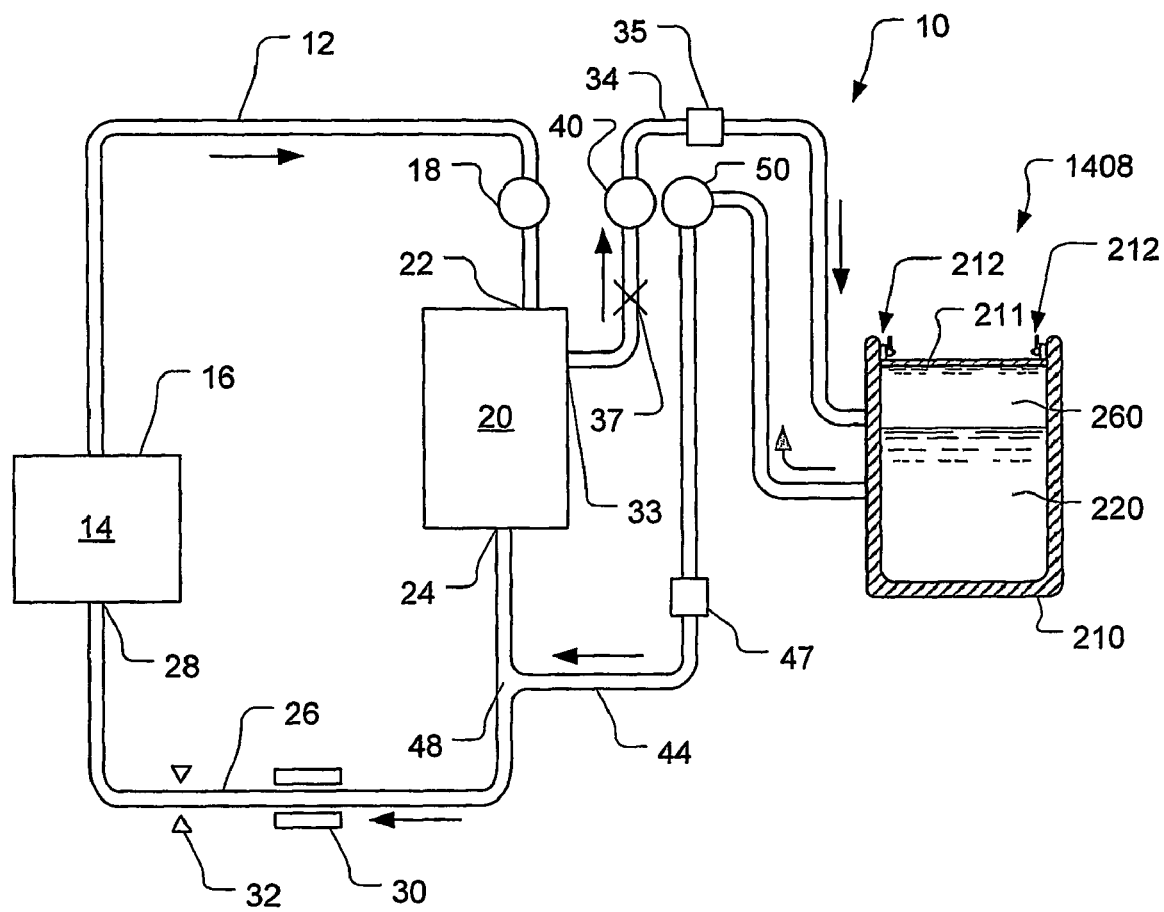

FIG. 26 illustrates waste balancing system 1408 implemented in blood treatment system 10. Waste balancing system 1408 includes container 210 enclosing flexible bag 220, flexible bag 260, and cap 211 held by clamps 212. Upon installation of waste balancing system 1408 in blood treatment system 10, cap 211 is fixed at a desired position in container 210 by clamps 212, thereby defining a fixed volume for the combination of flexible bag 220 and flexible bag 260. A mass of removed waste is added to flexible bag 260, forcing an equal mass of replacement fluid out of flexible bag 220 via conduit 44. The fixed volume assures that waste is not added to flexible bag 260 in a volume greater than the volume of replacement fluid that exits flexible bag 220.

Figure 27:
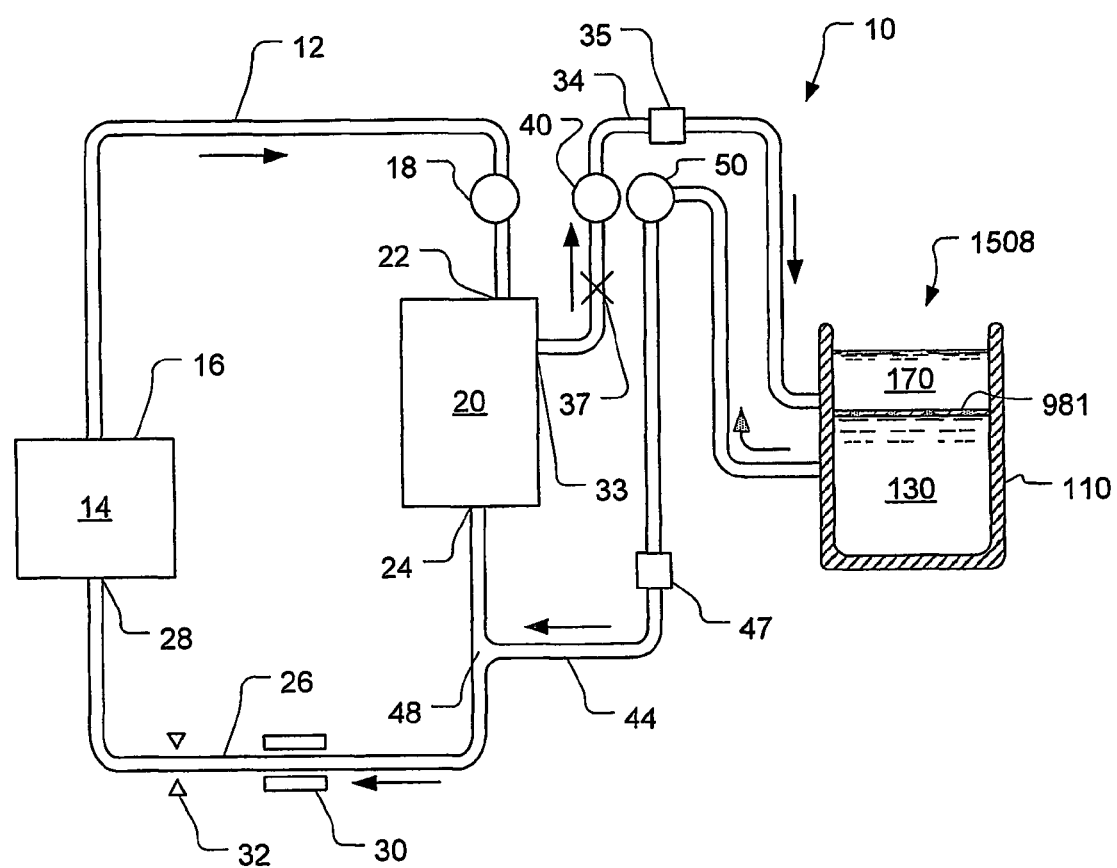

FIG. 27 illustrates waste balancing system 1508 implemented in blood treatment system 10. Waste balancing system 1508 comprises piston 981 sealed in slidable engagement within container 110. A mass of waste 170 added to container 110 via conduit 34 bears down on piston 981, causing piston 981 to slide downward in container 110 and force an equal mass of replacement fluid 130 to exit container 110 via conduit 44. Piston 981 may slide continuously between its illustrated position and the position shown in phantom. Piston 981 may alternately be replaced with a flexible diaphragm, for example.

Any of systems 108, 208, 308, 408, 508, 608, 708, 808, 908, 1008, 1108, 1208, 1308, 1408, and/or 1508, for example, may be used in waste balancing system 8 of the blood treatment system depicted in FIG. 10 or FIG. 22, for example.

Any of the alarms described herein may be transmitted from a patient's location to a remotely located monitor. For example, an alarm generated at a patient's home may be automatically transmitted over an electronic communications network to a remote medical or maintenance facility for appropriate attention. An alarm may indicate to a doctor at a hospital, for example, that a patient undergoing hemofiltration at home may be in danger of losing a net quantity of fluid greater than a desired ultrafiltration amount. This is exemplified in the Internet connection depicted in FIGS. 22, 23, 24, and 25. Or, an alarm may indicate to a service provider, for example, that a customer's blood treatment system needs more replacement fluid supply or other service.

Figure 28:
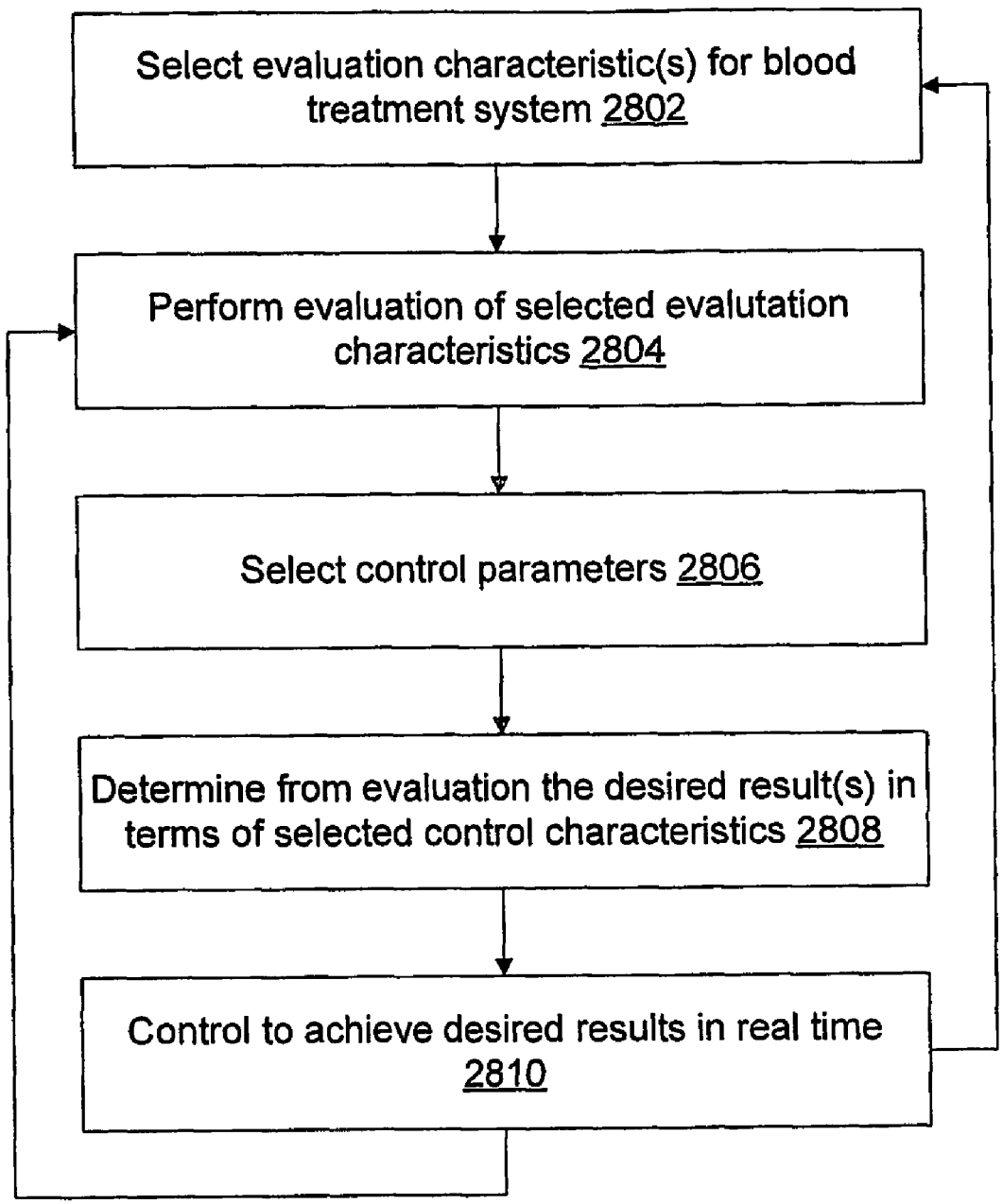
FIG. 28 is a flowchart of a method for a blood treatment system involving evaluation characteristics and control parameters.

FIG. 28 is a flowchart of a method 2800. Method 2800 may be performed automatically by an electronic controller. Alternatively, method 2800 may be performed manually by a patient at home. Method 2800 includes steps 2802, 2804, 2806, 2808, and 2810.

In step 2802, the method selects one or more evaluation characteristic(s) for a blood treatment system. This selection may be predetermined by a provider of the blood treatment system and hardwired, coded, or implemented mechanically, for example. Alternatively, the selection may be made by an operator or an electronic controller based on current conditions.

In step 2804, the method performs evaluation of the selected evaluation characteristic(s). This evaluation may be carried out automatically by electronic equipment connected to an electronic controller. Alternatively, the evaluation may be carried out automatically by mechanical equipment. Or, the evaluation may be carried out manually by a patient at home.

For example, if the selected evaluation characteristics include patient weight, the evaluation of step 2804 may be carried out automatically by a scale connected to an electronic controller. During the entire time the patient's blood is being treated, the patient may be seated on a platform containing a scale that continuously provides the patient's weight to an electronic controller.

In step 2806, the method selects control parameters. The selection may be made dynamically as a result of step 2802 and/or step 2804. For example, if accumulated waste volume is selected in step 2802 as an evaluation characteristic, step 2806 may select RF volume supplied as a control parameter. In another example, if step 2804 evaluates patient weight and finds it to be outside of a normal range, step 2806 may select multiple control parameters, such as RF volume supplied and RF mass supplied, as an additional safety measure.

In step 2808, the method determines from the evaluation of step 2804 the desired result(s) in terms of control parameters selected in step 2806. For example, if the evaluation of step 2804 determines that the patient weight is too high, step 2808 may determine that RF mass supplied should be less than accumulated waste mass by an amount equal to the patient's excess weight.

In step 2810, the method controls to achieve the desired result in real time, i.e., during a treatment session. For example, if the desired result is to supply RF mass that is a certain amount less than accumulated waste mass, the method may control a waste balancing system to supply RF mass in an amount less than accumulated waste mass. Method 2800 may return to step 2802 or 2804.

Any number of exemplary evaluation characteristics may be evaluated in order to determine a value for any number of exemplary control parameters. For example, fuzzy logic implemented in an electronic controller may determine that a certain combination of values determined upon evaluation of patient hydration, patient blood pressure, and patient temperature should result in controlling the alarm On/Off control parameter into an On state and the Treatment On/Off control parameter into an Off state. As another example, evaluation of the cleanliness of patient's blood and the desired treatment duration may determine an RF composition desired as a control parameter. Some exemplary evaluation characteristics may also be exemplary control parameters, and some exemplary control parameters may also be exemplary evaluation characteristics.

Figure 29:
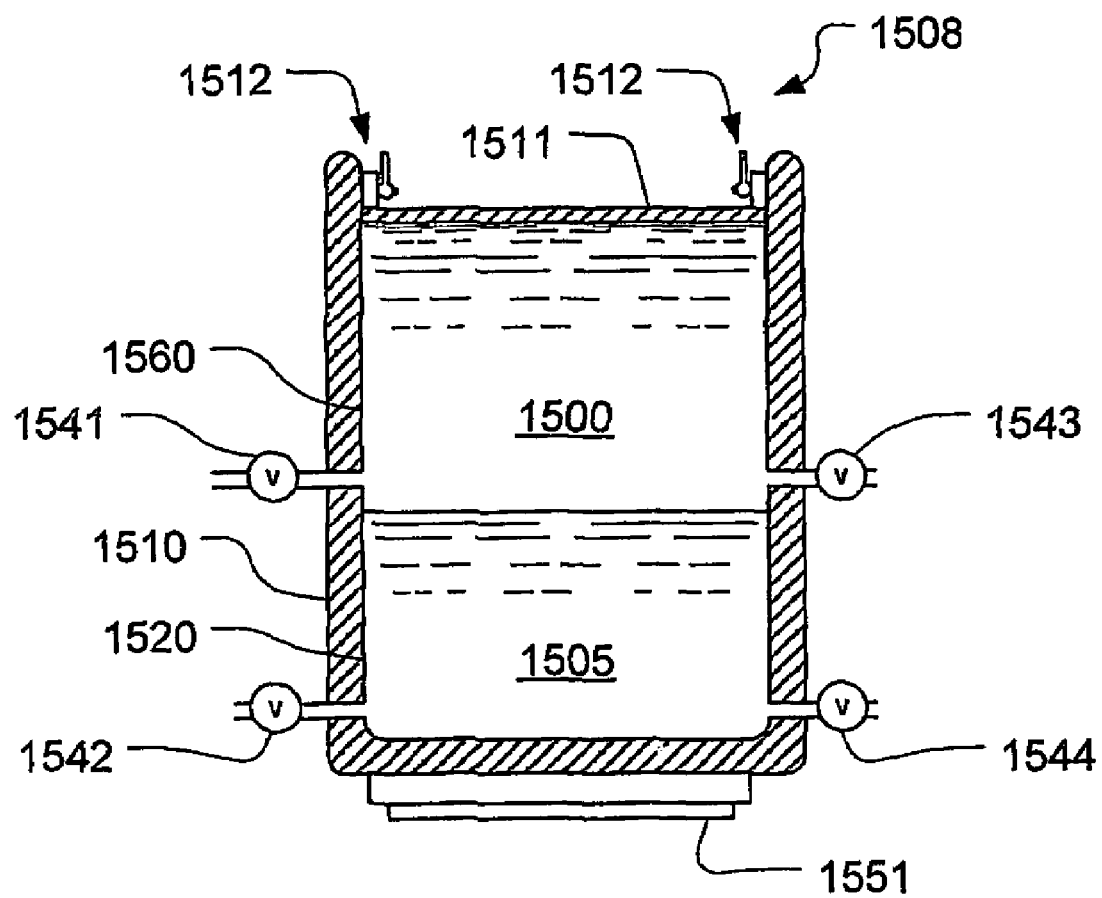
FIG. 29 illustrates an embodiment employing a combination of mass-sensing and fixed combined volume to provide for providing for net fluid balance of a patient during treatment.

Referring now to FIG. 29, a batch balancing device 1508 employs a single fixed volume vessel 1510 has an internal volume 1560 enclosing subvolumes 1500 and 1505 for replacement fluid and waste fluid respectively. The internal volume 1560 is fixed by means of a cap 1511 fixed by means of locks 1512 in a manner similar to that described with respect to foregoing embodiments. As waste fluid passes into subvolume 1505, an equal volume of replacement fluid may be forced out of subvolume 1500. Vessel 1510 may be large enough to contain an entire batch of replacement fluid for a treatment in the subvolume 1500 at the start of treatment. During treatment, the subvolume 1505 may fill with waste fluid and ultimately accommodate a volume resulting from an entire treatment. In this embodiment, therefore, no cycling of valves or pumps is required as each incremental volume of waste displaces a corresponding volume of replacement fluid progressively filling the subvolume 1505 and progressively emptying the subvolume 1500. The result of the above may therefore be a proper balancing of waste and replacement fluid over the course of an entire treatment with no required cyclic operation.

Valves 1541, 1542, 1543, and 1544 may be employed to initially fill subvolume 1500 and empty subvolume 1505 by appropriately opening and closing at appropriate times for filling and draining.

A refinement or alternative to the above is also illustrated: a scale 1551 may be employed to weigh an entire combined mass of replacement fluid and waste fluid to provide for constant fluid balance during treatment. In an embodiment relying solely on scale 1551, the cap 1511 and locks 1512 may not be required. During treatment, waste may be pumped into the subvolume 1505. This causes the total mass within the container 1510 to change unless replacement fluid is removed from subvolume 1500. A controller (not shown in FIG. 29) may control the flow of replacement fluid to maintain a constant total mass of the container 1510 and its contents in response to a weight indication from the scale 1551.

Constant volume and weight may be used in concert to control a single batch system as illustrated in FIG. 29. For example, weight may be used to provide an out-of-bounds signal to help guarantee the integrity of the constant volume system. More particularly, a controller may receive a signal from the scale and if the total mass goes out of a predefined range during treatment, an error condition may be indicated by the controller. Otherwise, the system may rely on the constant volume mechanism, in which replacement fluid is displaced by waste to maintain fluid balance during treatment.

In an alternative embodiment, a signal from the scale indicating total mass may be used continuously to adjust the flow rate of replacement fluid. For example, the flow of replacement fluid may be smoothed by biasing the rate of flow of replacement fluid generated by the constant volume mechanism according to a weight signal. Thus, for example, if the total mass indicated by the scale 1551 is offset from a predefined value the flow of replacement fluid may be increased or retarded by a controller that controls an assist pump (not shown, but preferably a non positive displacement type pump such as a centrifugal or turbine pump) in the replacement fluid outflow path. Thus, when an irregular flow results from the constant volume mechanism, it may be smoothed by data from the scale 1551. Such irregular flow may result, for example, due to irregular flexing of the flexible envelopes 1560 and 1520 containing the subvolumes 1500 and 1505. Yet another option is to switch to constant mass control using the weight as a signal to control replacement fluid flow when the weight varies from a range around a predefined value. Note that the predefined weight value may be set as the initial value before treatment begins.

Figure 30:
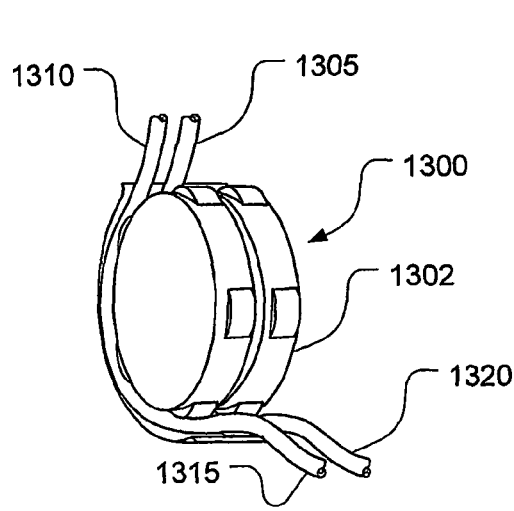
FIG. 30 illustrates a constant displacement mechanism for balancing waste and replacement fluid flows for maintaining net fluid balance of a patient during treatment.
Figure 31:
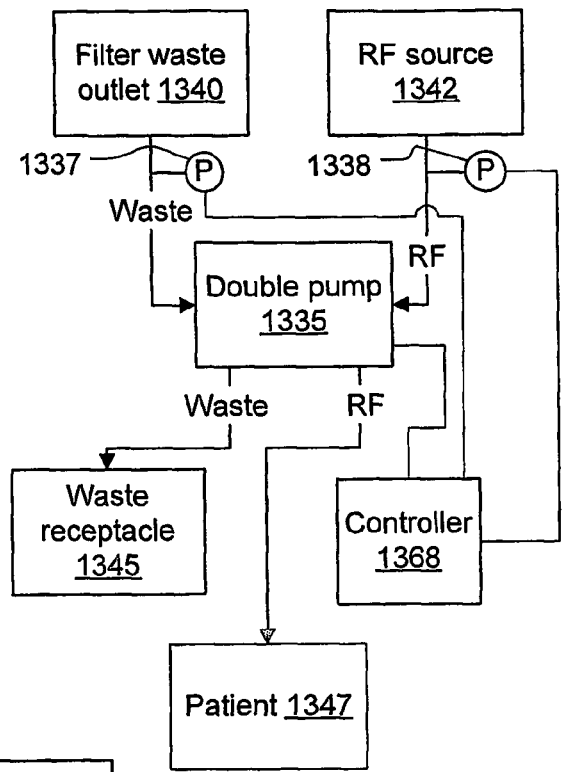
FIG. 31 illustrates an operating context for the device of FIG. 30.

Referring now to FIG. 30, a double peristaltic pump 1300 pumps waste fluid and replacement fluid through respective lines 1305 and 1310. The double peristaltic pump 1300 may consist of two pumps on a common shaft (the shaft is not explicitly illustrated) or may be rotated by a drive that provides for equal displacement rate of both the waste and replacement fluid streams flowing through lines 1305 and 1310. The double pump's 1300 rotor 1302 engages both lines 1305 and 1310 to pump fluid in each simultaneously and at rates that are proportional, since both pump rates are governed by the same shaft speed (i.e., that of the rotor 1302). The lines 1305 and 1310 may be identical and the rotor 1302 may be configured to engage them identically such that the rates of pumping in both lines 1305 and 1310 remain identical. As a result, the rate of flow of waste in one of the lines, say 1305, may be identical to a rate of flow of replacement fluid in the other line say 1310. FIG. 31 illustrates this context.

Referring now to FIG. 31, filter waste from a filter waste outlet 1340 is drawn by one line of a double pump 1335 which may be fashioned as illustrated and discussed with reference to FIG. 30. Simultaneously replacement fluid is pumped from a source 1342 through the other line of the double pump 1335. The replacement fluid may be pumped into a patient 1347 while waste is conveyed to a waste receptacle 1345. Note that the double pump 1335 may be of a type other than a peristaltic pump as illustrated in FIG. 30. For example, it may be of a non positive-displacement type such as a pair of turbine or centrifugal pumps driven by a common drive mechanism. Alternatively, it may be of a piston and cylinder, roots blower, diaphragm or other type of positive displacement pump. Preferably, the pump is of a type that allows for hermetic isolation of fluid contents.

Most types of pumps, including peristaltic pumps, are characterized by pumping rates that are not perfectly proportional to rotor speed but rather to both rotor speed and pumping head. Thus, pressure of the waste and replacement fluid lines may be measured at a pump-inlet, pump-outlet, or both by pressure sensors as indicated at 1337 and 1338. The latter indicate pressure sensing at pump-inlet locations. A controller 1368 may control the pump speed or otherwise control the pumping rate so as not to generate a pressure difference across the double pump 1335 that is determined to correspond to equal flow rate through both the RF and waste lines. Thus, if the pressure at the inlet (illustrated) or pressure drop (not illustrated, but pressure-difference transducers could be used with taps at points upstream and downstream of the double pump 1335 or an additional set of pressure sensors located downstream of the double pump 1335 could be used) could be determined by the controller and if it ran above a predetermined value, the pump rate could be slowed (e.g., by reducing the rotor speed of a peristaltic pump as illustrated in FIG. 30) and if it dropped too low, the rate could be increased. Note that only an upper limit may be employed rather than an allowed band of pressure differences. Alternatively, the controller may halt treatment if the pressure head goes outside a predefined range. Alternatively, control valves (not shown) may be used to equalize the head across both portions of the double pump 1335 to ensure that flow rates will tend toward identity.

Figure 32:
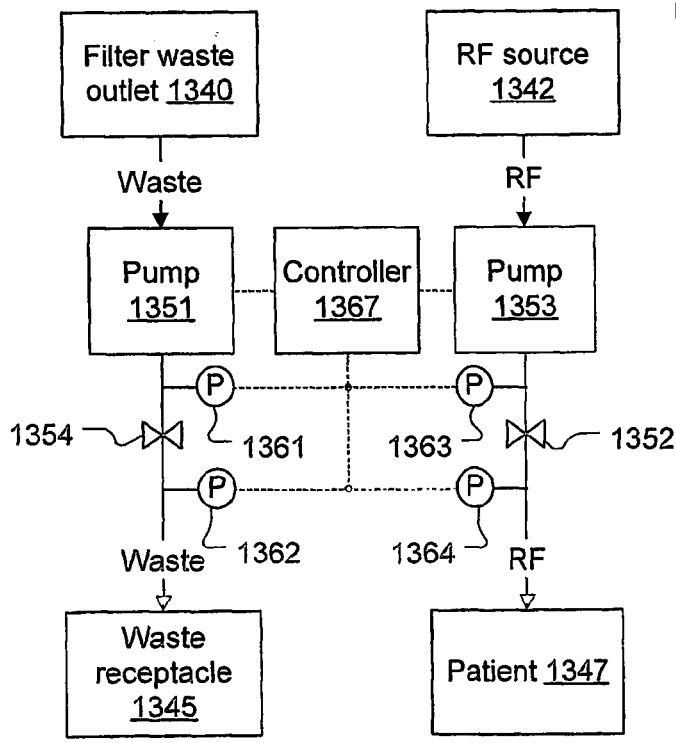
FIG. 32 illustrates a two-pump mechanism for maintaining fluid balance of a patient during treatment.

FIG. 32 illustrates another mechanism for controlling the rate of flow of replacement fluid such that it remains nearly identical to the rate of flow of waste removal. The configuration of FIG. 32 is similar to that of FIG. 31 except that instead of a single double pump 1335 (FIG. 31) separate pumps 1351 and 1353 are used for pumping waste and replacement fluid respectively. Respective throttling valves 1354 and 1352 in each fluid line create a pressure difference on either side thereof that is measured by respective pressure sensors 1361, 1363, 1362, and 1364. The latter apply pressure signals to a controller 1367 which regulates the pumping speed of the two pumps 1351 and 1353 to provide for identical (or a desired departure from identical rates as indicated by treatment requirements) flow rate of replacement fluid added to the patient 1347 and waste fluid drawn from a filter outlet 1340. In effect, the throttling valves 1354 and 1352 and pressure sensors 1361, 1362, 1352 and 1364 are used for flow measurement whereby the throttling of the flow and the pressure indicate flow rate according to a pressure drop versus flow rate curve which may be derived by suitable calibration. A curve may be include other parameters such as fluid temperature and density indicated by concentration sensors and temperature sensors.

Figure 33:
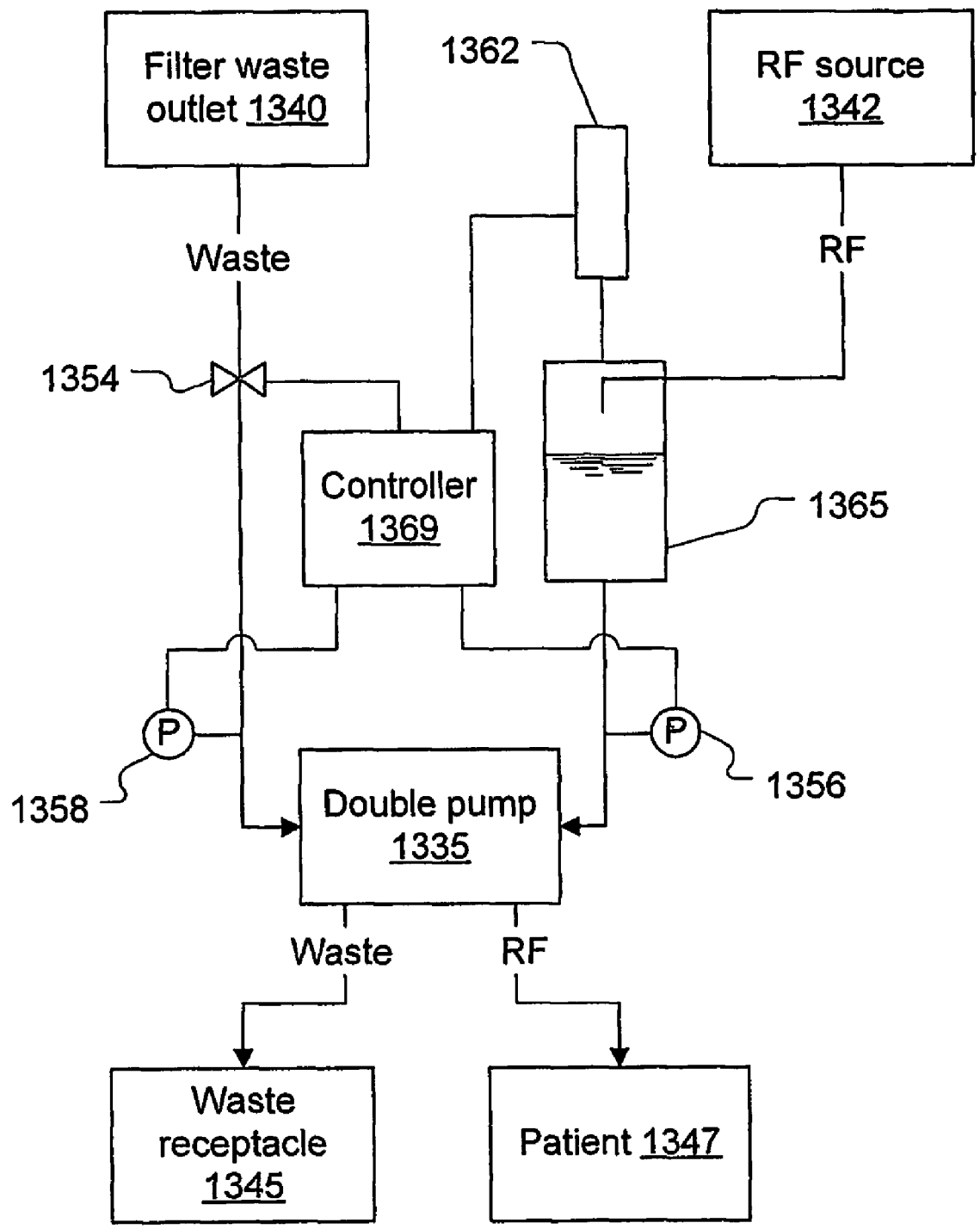
FIG. 33 illustrates another operating context for the device of FIG. 30.

Referring to FIG. 33, pressure differential across the double pump 1335 (pump head) may be controlled by a controller. In FIG. 33, two additional mechanisms are illustrated for controlling the pumping head of the double pump 1335. In a first, a variable throttling valve 1354 is controlled by a controller 1369 responsively to one or more pressure sensors exemplified by pressure sensors 1358 and 1356 located upstream of the double pump 1335. The variable throttling valve 1354 may vary the pump head of the double pump 1335 on the filter waste side such that a desired parity with the head across the replacement fluid side is achieved. Note that pressure sensors may be used downstream of the double pump 1335 alternatively, or in addition to, the pressure sensors 1358 and 1356 to determine pressure head. Also, differential pressure transducers may be used with upstream and downstream taps. Moreover, a variable throttling valve may be used downstream of the double pump 1335 rather than upstream. The throttling may be done on the replacement fluid side alternatively or in addition to throttling on the waste fluid side as illustrated.

Illustrated on the replacement fluid side is a linear actuator 1362 which is controlled to raise and lower a drip tank 1365. Fluid from the replacement fluid source 1342 is supplied td the drip tank 1365 and the height of the fluid column can be varied by the linear actuator 1362 by raising and lowering the drip tank 1365. As a result, the controller 1369 is able to vary the inlet pressure sensed at the pressure sensor 1356. By controlling the pressure of one side of the double pump 1335, it may be possible to provide a desired pressure head across the double pump 1335 to ensure that both the replacement fluid side and waste fluid side are substantially equal or such that they differ by an amount that ensures the total fluid balance during a treatment is at a desired level, for example, such that the volume of replacement fluid added to the patient is equal to the volume of waste fluid removed.

Figure 34:
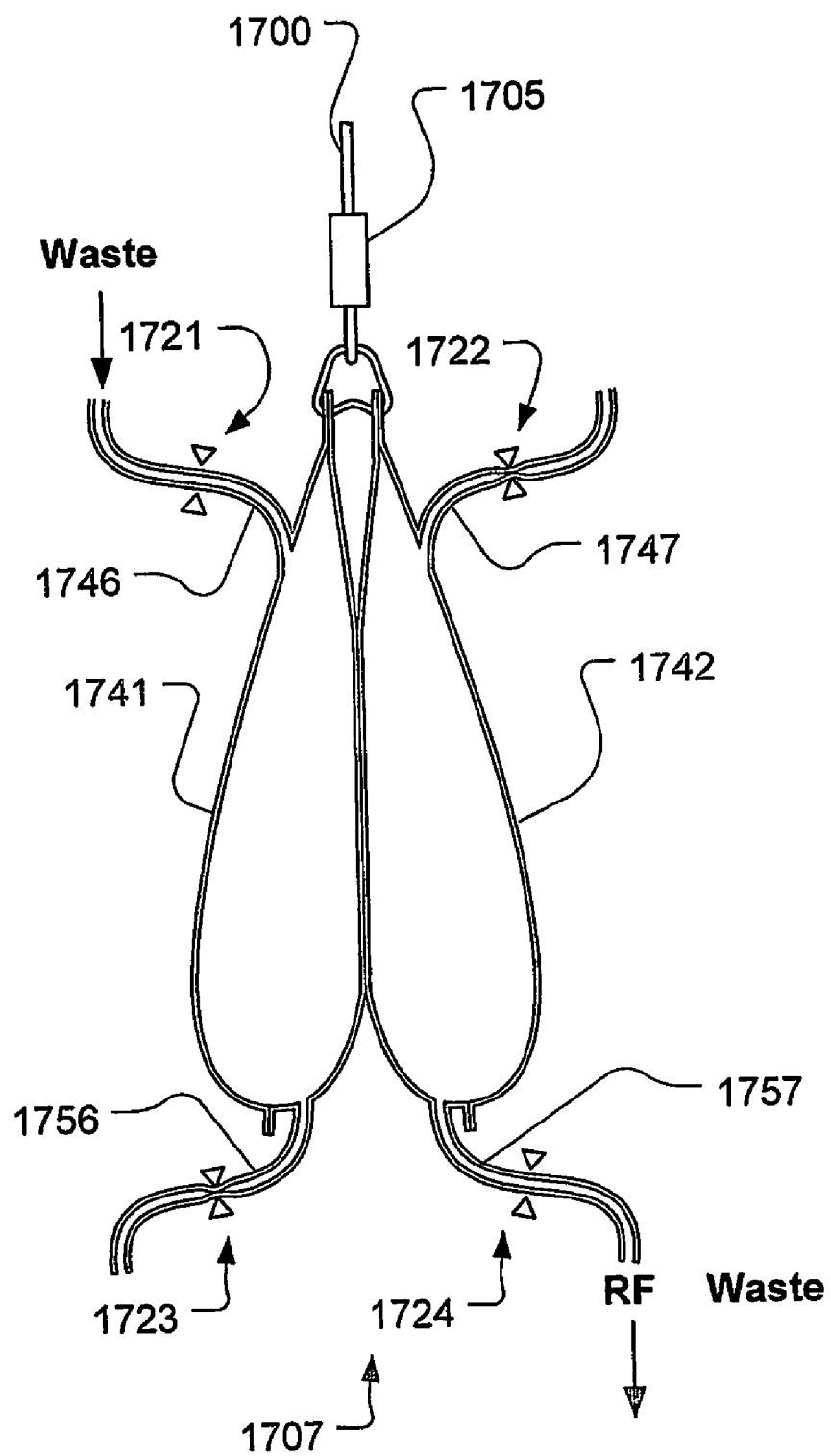
FIG. 34 illustrates a constant combined mass mechanism for maintaining fluid balance of a patient during treatment.

Referring now to FIG. 34, a mass-balancing system 1707 for maintaining patient fluid balance is illustrated. Here, waste flows into a waste bag 1741 through an inlet tube 1746. Access to the inlet tube 1746 may be controlled by a valve 1721. An outlet tube 1756 may be used to release the contents of the waste bag 1741 via a valve 1723. Replacement fluid flows into a replacement fluid bag 1741 through an inlet tube 1747. Access to the inlet tube 1747 may be controlled by a valve 1722. An outlet tube 1757 may be used to release the contents of the replacement fluid bag 1742 via a valve 1724. The total mass of the bags 1741 and 1742 and their contents is indicated by a scale 1705 and hung from a fixed hanger 1700.

At the start of treatment, the control valve 1723 may be opened and the control valve 1721 closed to permit the emptying of the waste fluid bag 1741. Also, the control valve 1722 may be opened and the control valve 1724 closed to permit the filling of the replacement fluid bag 1741 with replacement fluid. Prior to treatment, a reading from the scale 1705 may be obtained and stored by a controller (not shown separately). The controller may then control the control valves 1721, 1722, 1723, and 1724 as well as any pumps employed, depending on the particular design of the treatment system, to fill the waste fluid bag 1741 with waste fluid and move replacement fluid out of the replacement fluid bag 1742 at such rate as will maintain a constant value of the mass indicated by the scale 1705. The bags 1741 and 1742 may be large enough to accommodate that waste and replacement fluid loads for an entire treatment.

Alternatively, the control valves 1721, 1722, 1723, and 1724 (and any pumps required—not shown) may be actuated to periodically empty the waste fluid bag 1741 and refill the replacement fluid bag 1742 to perform a cyclic balancing similar to that described with reference to FIG. 29. That is, after a certain interval measured by elapsed time, cumulative flow of replacement or waste fluid indicated by the integrated signal of one or more flow sensors, rotations of the rotor of a replacement fluid or waste fluid pump, etc. the waste fluid bag 1741 may be emptied by actuation of the control valves 1721 and 1723 and the replacement fluid bag 1742 re-filled by actuation of the control valves 1722 and 1724. During such a reset operation, the treatment may be halted to stop the flow of waste fluid from a filter or dialyzer. Alternatively, a buffer vessel may be provided and used to allow the system of FIG. 34 to reset itself while waste fluid continues to collect in the buffer vessel. Once reset, the waste fluid bag 1741 would fill with the contents of the buffer vessel.

Note that although many of the above embodiments are described in terms of identical rates of replacement fluid addition and waste fluid removal, it is recognized that during most treatments a certain net addition or removal of waste fluid may be required (ultrafiltrate). Thus, it is contemplated in all of the contexts described that a net fluid addition or removal may be accomplished by various means, such as adding a certain amount of fluid at a point during treatment and otherwise maintaining equal rates of fluid removal and addition. Alternatively, the rates may be biased to favor replacement fluid addition or fluid removal according to the indicated requirements for a treatment. For example, referring to FIG. 1, level sensor 164A may indicate by magnitude of a signal level the height of the top of the container 160. This signal level may be biased to allow a desired amount of over-filling or under-filling to occur, which may result in a net extraction of fluid. In the embodiment of FIG. 7, the level of the tube 652 may be altered to favor net extraction or net addition of fluid. The pressure signal of a pressure-based control mechanism, for example that of FIG. 3, may be biased also to provide for net addition or extraction of fluid. Various mechanisms may be provided to allow for net addition or extraction as required and in no instance is it suggested that net extraction or addition is required to be zero, even though the embodiments above may be discussed in the context of zero net fluid addition/extraction by way of example.

It will be clear to one of skill in the art that the balancing systems described are as applicable to hemodialysis, hemodiafiltration, and other blood treatment systems as they are to hemofiltration, which is the particular embodiment emphasized in the detailed description. To be clear, in a dialysis system, the flow of dialysate is across one side of a filter membrane and the inflow of dialysate and outflow of dialysate are the flows that are balanced by the balancing mechanism. Thus, in the embodiments above, and in the claims, where the term "waste" is used, it should be clear that this may refer to the "spent" dialysate as much as fluid filtered out of the blood as in a hemofiltration system. Correspondingly, it should also be clear that the term "replacement fluid" may be understood to refer, depending on the embodiment, to fresh dialysate as well as a fluid infusate, as would be employed in a pure hemofiltration system. Also, perfect balance is usually not the goal in a treatment, as is known by those skilled in the art. The goal during treatment usually includes a net reduction and sometimes a net addition of fluid to a patient. Various mechanisms for providing this, for example with metered bypass flows of waste or replacement fluid to bias the balancing system or such are well-known.

One of ordinary skill in the art will recognize from the disclosure herein a number of permutations and alterations to the exemplary embodiments. Therefore, the invention is not limited by the particular embodiments disclosed.

The invention claimed is:

1. A waste balancing system for medical use comprising:
   a first container containing a fluid waste;
   a second container containing a replacement fluid;
   a support supporting the first and second containers in a stacked relationship such that the weight of one of the first and second containers bears on the other of the first and second containers,
   the first and second containers having flexible walls in direct contact with each other such that said containers form a column of fluid which conforms to the shape and size of the support; and
   a pressure sensor in pressure communication with at least one of the first and second containers and located at a bottom of the support such that the pressure sensor indicates a height of the column of fluid;
   a controller connected to control a pump and to receive a signal from said pressure sensor and control a rate of flow of at least one of said fluid waste and said replacement fluid to and from said first and second containers responsively to said signal, such that a constant height of the column of fluid is maintained and thereby maintaining a constant total mass of fluid in both of the first and second containers combined.

2. The waste balancing system of claim 1, further comprising a detector configured to detect an emptying of one of said first and second containers, said controller being configured to control said flow responsively to said detector by emptying waste from the first container and adding replacement fluid to the second container in such a manner that the height of the column of fluid is achieved.

3. The waste balancing system of claim 1, wherein the first container is stacked on top of the second container and the support defines a vessel with rigid walls in which the first and second containers rest.

4. The waste balancing system of claim 1, wherein the pressure sensor is adjustable.

5. The waste balancing system of claim 1, wherein the pressure sensor is operatively connected to an outlet of one of the first and second containers.

6. A blood treatment system comprising:
   blood treatment means for clearing a patient's blood of toxins;
   a fluid balancing system comprising:
      a first flexible container means containing a fluid waste;
      a second flexible container means containing a replacement fluid;
   a support supporting the first and second container means in cooperating relationship such that a pressure in at least one of said first and second container means is indicative of a combined weight of said first and second container means with their respective contents;
   a pressure sensor in pressure communication with at least one of the first and second container means;
   a blood treatment machine and a conduit connectable to the blood treatment machine; and
   a controller configured to control a rate of flow of replacement fluid responsively to the pressure sensor such that a combined weight of the first and second container means is maintained at a constant level, whereby a flow from one of the first and second containers means is offset by a flow into the other of the first and second container means.

7. The blood treatment system of claim 6, wherein the blood treatment machine comprises a hemofilter.

8. The blood treatment system of claim 6, wherein the blood treatment machine comprises a dialyzer.

9. The blood treatment system of claim 6, further comprising a removable disposable cartridge containing at least part of the first container means as an integral part of the removable disposable cartridge.

10. The waste balancing system of claim 6, wherein the first container means includes an expandable container.

11. The blood treatment system of claim 6, wherein the pressure sensor is operatively connected to an outlet of one of the first and second flexible container means.

12. A blood treatment system comprising:
   blood treatment means for clearing a patient's blood of toxins;

a fluid balancing system comprising:
- a first container containing a fluid waste;
- a second container containing a replacement fluid;
- a support supporting the first and second containers in cooperating relationship such that a pressure in at least one of said first and second containers is indicative of a combined weight of said first and second containers with their respective contents;
- a pressure sensor in pressure communication with at least one of the first and second containers;
- a blood treatment machine and a conduit connectable to the blood treatment machine;
- a controller configured to control a rate of flow of replacement fluid responsively to the pressure sensor; and
- a piston separating the first and second containers.

* * * * *